(12) United States Patent
Kanada

(10) Patent No.: US 11,854,190 B2
(45) Date of Patent: Dec. 26, 2023

(54) SIMILARITY DETERMINATION APPARATUS, SIMILARITY DETERMINATION METHOD, AND SIMILARITY DETERMINATION PROGRAM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 425 days.

(21) Appl. No.: 17/167,058

(22) Filed: Feb. 3, 2021

(65) Prior Publication Data
US 2021/0166382 A1 Jun. 3, 2021

Related U.S. Application Data

(63) Continuation of application No. PCT/JP2019/023814, filed on Jun. 17, 2019.

(30) Foreign Application Priority Data

Aug. 31, 2018 (JP) .................................. 2018-162860

(51) Int. Cl.
*G06T 7/00* (2017.01)
*G06T 7/11* (2017.01)
(Continued)

(52) U.S. Cl.
CPC ............ *G06T 7/0012* (2013.01); *G06F 18/22* (2023.01); *G06T 7/11* (2017.01); *G06V 10/25* (2022.01);
(Continued)

(58) Field of Classification Search
CPC ...................... G06T 7/0012; G06T 7/11; G06T 2207/30061; G06T 2200/24;
(Continued)

(56) References Cited

U.S. PATENT DOCUMENTS 7,783,096 B2 * 8/2010 Chen ....................... G06T 7/207
                                                      382/128
7,848,592 B2 * 12/2010 Chen ......................... G06T 7/35
                                                      382/128
(Continued)

FOREIGN PATENT DOCUMENTS

CN    102208105    10/2011
CN    106164903    11/2016
(Continued)

OTHER PUBLICATIONS

Adrien Depeursinge et al., "Case-based lung image categorization and retrieval for interstitial lung diseases: clinical workflows", Int J Comput Assist Radiol Surg., Jun. 1, 2011, pp. 97-110.
(Continued)

*Primary Examiner* — Juan A Torres
(74) *Attorney, Agent, or Firm* — JCIPRNET

(57) ABSTRACT

A region division unit divides a target region of a first medical image into a plurality of regions. A finding classification unit classifies each pixel of the first medical image into at least one finding. A feature amount calculation unit calculates a first feature amount for each finding. A region similarity derivation unit derives a region similarity between the first medical image and a second medical image for each of the divided regions. A similarity derivation unit performs a weighting operation for a plurality of region similarities with a weighting coefficient corresponding to at least one of a size of each of the divided regions or a size of a specific finding included in each of the divided regions to derive a similarity between the first medical image and the second medical image.

20 Claims, 18 Drawing Sheets

(51) Int. Cl.
*G06V 10/25* (2022.01)
*G06V 10/75* (2022.01)
*G06F 18/22* (2023.01)
*G06V 10/74* (2022.01)
*G06V 20/64* (2022.01)

(52) U.S. Cl.
CPC .......... *G06V 10/751* (2022.01); *G06V 10/761* (2022.01); *G06V 20/653* (2022.01); *G06T 2207/30061* (2013.01); *G06V 2201/031* (2022.01)

(58) Field of Classification Search
CPC . G06T 2207/10081; G06T 2207/10088; G06T 2207/20084; G06F 18/22; G06V 10/25; G06V 10/751; G06V 10/761; G06V 20/653; G06V 2201/031; A61B 5/055; A61B 6/03
USPC ....................................................... 382/128
See application file for complete search history.

(56) References Cited

U.S. PATENT DOCUMENTS

| | | | |
|---|---|---|---|
| 8,605,978 B2 | 12/2013 | Mizuno | |
| 8,958,613 B2 | 2/2015 | Kondo et al. | |
| 9,741,114 B2 * | 8/2017 | Varkuti | A61B 6/032 |
| 9,852,269 B2 * | 12/2017 | Sakagawa | G16H 30/20 |
| 10,055,543 B2 | 8/2018 | Kozuka et al. | |
| 10,839,511 B2 | 11/2020 | Oosawa | |
| 10,930,396 B2 | 2/2021 | Kanada | |
| 2002/0065460 A1 | 5/2002 | Murao | |
| 2010/0076921 A1 | 3/2010 | Kato et al. | |

FOREIGN PATENT DOCUMENTS

| | | |
|---|---|---|
| CN | 106560827 | 4/2017 |
| JP | 2000342558 | 12/2000 |
| JP | 2001117936 | 4/2001 |
| JP | 2002230518 | 8/2002 |
| JP | 2010079398 | 4/2010 |
| JP | 2011118543 | 6/2011 |
| WO | 2013065090 | 5/2013 |
| WO | 2018116727 | 6/2018 |

OTHER PUBLICATIONS

Joseph Jacob et al., "Evaluation of computer-based computer tomography stratification against outcome models in connective tissue disease-related interstitial lung disease: a patient outcome study", BMC Medicine, Nov. 23, 2016, pp. 1-13.

Iwasawa Tae et al., "Quantitative Evaluation of CT Images of Interstitial Pneumonia by Computer", Japanese Journal of Tomography, Aug. 2014, pp. 1-11.

"International Search Report (Form PCT/ISA/210) of PCT/JP2019/023814," dated Sep. 10, 2019, with English translation thereof, pp. 1-3.

Written Opinion of the International Searching Authority (Form PCT/ISA/237) of PCT/JP2019/023814, dated Sep. 10, 2019, with English translation thereof, pp. 1-7.

"Office Action of China Counterpart Application", dated Sep. 20, 2023, with English translation thereof, p. 1-p. 19.

* cited by examiner

FIG. 11

| TYPE OF FINDING | EVALUATION VALUE |
|---|---|
| INFILTRATIVE SHADOW | 2.9 |
| GROUND-GLASS SHADOW | 7.6 |
| RETICULAR SHADOW | 8.5 (MAXIMUM) |
| BRONCHODILATATION | 3.2 |
| . . . | . . . |
| . . . | . . . |
| NORMAL LUNG | −7.1 |
| LOW ABSORPTION AREA (EMPHYSEMA) | −12.3 |

| TYPE OF FINDING | VOLUME |
|---|---|
| GROUND-GLASS SHADOW | 20540 |
| INFILTRATIVE SHADOW | 11210 |
| LOW ABSORPTION AREA | 2890 |
| BRONCHODILATATION | 4030 |
| RETICULAR SHADOW | 9680 |
| CYST | 1430 |
| NORMAL LUNG | 157830 |

| CASE IMAGE | SIMILARITY |
|---|---|
| IMG0012.dcm | 0.87 |
| IMG0254.dcm | 0.77 |
| IMG0123.dcm | 0.54 |
| IMG0022.dcm | 0.52 |

FIG. 18

| TYPE OF FINDING | REGION PATTERN | | |
|---|---|---|---|
| | FIRST | SECOND | SIXTH |
| GROUND-GLASS SHADOW | 0.7 | 0.3 | 0 |
| RETICULAR SHADOW | 0.7 | 0.3 | 0 |
| PUNCTATE SHADOW | 0.3 | 0.4 | 0.3 |
| NODULAR SHADOW | 0 | 0.5 | 0.5 |
| . . . | | | |

FIG. 19

| TYPE OF FINDING | REGION PATTERN | | |
| --- | --- | --- | --- |
| | FIRST | SECOND | SIXTH |
| GROUND-GLASS SHADOW | 1.0 | 0 | 0 |
| RETICULAR SHADOW | 1.0 | 0 | 0 |
| PUNCTATE SHADOW | 0.7 | 0.3 | 0 |
| NODULAR SHADOW | 0.5 | 0.5 | 0 |
| ... | | | |

FIG. 20

| TYPE OF FINDING | REGION PATTERN | | |
|---|---|---|---|
| | FIRST | SECOND | SIXTH |
| GROUND-GLASS SHADOW | 0 | 0.7 | 0.3 |
| RETICULAR SHADOW | 0 | 0.7 | 0.3 |
| PUNCTATE SHADOW | 0 | 0.3 | 0.7 |
| NODULAR SHADOW | 0 | 0 | 1.0 |
| . . . | | | |

SIMILARITY DETERMINATION APPARATUS, SIMILARITY DETERMINATION METHOD, AND SIMILARITY DETERMINATION PROGRAM

CROSS-REFERENCE TO RELATED APPLICATIONS

This application is a Continuation of PCT International Application No. PCT/JP2019/023814 filed on Jun. 17, 2019, which claims priority under 35 U.S.C § 119(a) to Japanese Patent Application No. 2018-162860 filed on Aug. 31, 2018. Each of the above application(s) is hereby expressly incorporated by reference, in its entirety, into the present application.

BACKGROUND OF THE INVENTION

1. Field of the Invention

The present disclosure relates to a similarity determination apparatus, a similarity determination method, and a non-transitory computer readable recording medium storing a similarity determination program that determine a similarity between two medical images.

2. Description of the Related Art

In recent years, with the progress of medical apparatuses, such as a computed tomography (CT) apparatus and a magnetic resonance imaging (MM) apparatus, high-resolution three-dimensional images with higher quality have been used for image diagnosis.

In the medical field, a similar case search apparatus has been known which searches for past cases similar to an examination image, such as a CT image to be examined, on the basis of the examination image (for example, see Case-based lung image categorization and retrieval For interstitial lung diseases: clinical workflow, Adrien Depeursinge et al., Int J CARS (2012) 7:97-110, Published online: 1 Jun. 2011, JP2013-065090A, and JP2011-118543A). Case-based lung image categorization and retrieval for interstitial lung diseases: clinical workflows, Adrien Depeursinge et al., Int J CARS (2012) 7:97-110, Published online: 1 Jun. 2011 discloses a method which classifies a case image of the lung into a plurality of regions indicating a plurality of types of tissues or lesions (hereinafter, it is assumed that tissues or lesions are generically referred to as findings), registers the plurality of regions in a case database, similarly classifies an examination image of the lung into a plurality of regions indicating a plurality of types of findings, and searches for a case image similar to the examination image on the basis of the classification result of the findings for the examination image. In addition, JP2013-065090A and JP2011-118543A disclose a method which compares a feature amount of an image, such as a density histogram of the image, the average of density, or a variance of density, with a feature amount of an image registered in a database to search for an image similar to an examination image. Further, as a method for calculating the similarity between images, a method has been proposed which sets a plurality of partial regions in at least one of a plurality of images, determines the similarity between each of the set partial regions and each corresponding region in other images, and weights and adds the determined similarities between the partial regions using a weighting coefficient set for each partial region to calculate the overall region similarity (see JP2000-342558A).

However, interstitial pneumonia is known as a lung disease. A method has been proposed which analyzes a CT image of a patient with interstitial pneumonia, and classifies and quantifies lesions indicating specific findings, such as honeycomb lung, a reticular shadow, and a cyst included in the CT image (see Evaluation of computer-based computer tomography stratification against outcome models in connective tissue disease-related interstitial lung disease: a patient outcome study, Joseph Jacobi et al., BMC Medicine (2016) 14:190, DOI 10.1186/s12916-016-0739-7 and Quantitative Evaluation of CT Images of Interstitial Pneumonia by Computer, Iwasawa Tae, Japanese Journal of Tomography, vol. 41, No. 2, August 2014). The method which analyzes a CT image and classifies and quantifies lesions makes it possible to easily determine the degree of lung disease. In addition, different colors are assigned to the classified and quantified regions and the regions are displayed, which makes it possible to easily diagnose how much a specific symptom region is included in the image.

Further, it is necessary to detect a structure in a three-dimensional image in order to extract a structure, such as an organ of interest, from a three-dimensional image such as a CT image. Here, a deep learning method has been proposed in order to classify the pixels of interest in an image into a plurality of classes. Deep learning is a machine learning method using a multi-layer neural network constructed by hierarchically connecting a plurality of processing layers.

In deep learning, in each layer of the multi-layer neural network, arithmetic processing is performed for a plurality of different arithmetic result data items obtained by the previous layer for input data, that is, data of the extraction result of feature amounts. Then, in the subsequent processing layers, arithmetic processing is further performed for the obtained data of the feature amounts to improve the recognition rate of the feature amounts, and the input data can be classified into a plurality of classes.

It is considered that the deep learning method is applied to the above-mentioned three-dimensional image to classify each pixel of the three-dimensional image into a plurality of classes. For example, in a case in which a plurality of types of structures included in a three-dimensional image are classified, deep learning is performed for a neural network, using a three-dimensional image as an input, such that the pixel to be processed in the three-dimensional image is classified into any one of a plurality of types of structures. The use of the neural network subjected to deep learning makes it possible to classify a pixel to be processed of the input three-dimensional image into any one of the plurality of types of structures.

SUMMARY OF THE INVENTION

The methods disclosed in Case-based lung image categorization and retrieval For interstitial lung diseases: clinical workflow, Adrien Depeursinge et al., Int J CARS (2012) 7:97-110, Published online: 1 Jun. 2011, JP2013-065090A, JP2011-118543A, and JP2000-342558A are used to search for a case image including a lesion similar to that in the lung in the examination image. In contrast, the findings included in the examination image tend to occur in a specific region according to their features. Therefore, in a case in which the similarity between the examination image and the case image is determined, it is important to consider the position and distribution of findings in a target organ included in the examination image.

The present disclosure has been made in view of the above-mentioned problems and an object of the present disclosure is to appropriately determine a similarity between images on the basis of the position and distribution of findings included in the images.

According to the present disclosure, there is provided a similarity determination apparatus that determines a similarity between a first medical image and a second medical image. The similarity determination apparatus comprises: a region division unit that divides a target region of the first medical image into a plurality of regions; a finding classification unit that classifies each pixel of the first medical image into at least one finding; a feature amount calculation unit that calculates a first feature amount for each finding classified in the first medical image for each of the divided regions; a region similarity derivation unit that derives a region similarity between the first medical image and the second medical image for each of the divided regions, on the basis of the first feature amount for each finding calculated in the first medical image and a second feature amount for each finding calculated in advance in the second medical image; and a similarity derivation unit that performs a weighting operation for a plurality of the region similarities with a weighting coefficient corresponding to at least one of a size of each of the divided regions or a size of a specific finding included in each of the divided regions to derive a similarity between the first medical image and the second medical image.

In addition, in the similarity determination apparatus according to the present disclosure, the region division unit may divide the target region into a plurality of regions for each of a plurality of different types of region patterns, on the basis of the region patterns. The feature amount calculation unit may calculate the first feature amount for each of the divided regions for each of the region patterns. The region similarity derivation unit may derive the region similarity for each of the divided regions for each of the region patterns. The similarity derivation unit may perform the weighting operation for the region similarities for the plurality of types of region patterns to derive the similarity between the first medical image and the second medical image.

Further, in the similarity determination apparatus according to the present disclosure, the similarity derivation unit may perform the weighting operation for the region similarities for the plurality of types of region patterns using the weighting coefficient and a region pattern weighting coefficient corresponding to a type of the finding and a type of the region pattern.

Furthermore, the similarity determination apparatus according to the present disclosure may further comprise an input unit that receives a command to change the region pattern weighting coefficient. The similarity derivation unit may perform the weighting operation using the weighting coefficient and the changed region pattern weighting coefficient.

Moreover, in the similarity determination apparatus according to the present disclosure, the specific finding may be a finding of a lesion.

In addition, in the similarity determination apparatus according to the present disclosure, the finding classification unit may include a discriminator that has been subjected to machine learning so as to classify a plurality of types of the findings and classify each pixel of the first medical image into at least one of the plurality of types of findings using the discriminator.

Further, the similarity determination apparatus according to the present disclosure may further comprise a search unit that searches for the second medical image similar to the first medical image as a similar medical image on the basis of similarities between the first medical image and a plurality of second medical images with reference to a case database in which the plurality of second medical images are registered and the second feature amounts for each of the plurality of second medical images are registered so as to be associated with each of the plurality of second medical images.

Furthermore, the similarity determination apparatus according to the present disclosure may further comprise a display control unit that displays a search result of the similar medical image on a display unit.

Moreover, in the similarity determination apparatus according to the present disclosure, in a case in which the first medical image and the second medical image include a lung and the target region is a lung region, the region division unit may extract a bronchus from the lung region and divide the lung region into a plurality of regions on the basis of a position of the bronchus.

In addition, in the similarity determination apparatus according to the present disclosure, the region division unit may specify a plurality of branch positions of the bronchus and divide the lung region into a plurality of regions on the basis of the branch positions.

Further, in the similarity determination apparatus according to the present disclosure, the region division unit may divide the lung region into a plurality of regions in a vertical direction on the basis of the branch positions.

The "vertical direction" means the direction of the body axis of a patient who is the subject from which the medical image has been acquired.

Furthermore, in the similarity determination apparatus according to the present disclosure, the region division unit may divide the lung region into a region within a specific distance from a specific branch position among the plurality of branch positions and a region other than the region within the specific distance.

Moreover, in the similarity determination apparatus according to the present disclosure, the region division unit may further divide the lung region into an outer region and an inner region.

In addition, in the similarity determination apparatus according to the present disclosure, the region division unit may further divide the lung region into a dorsal region and a ventral region.

According to the present disclosure, there is provided a similarity determination method for determining a similarity between a first medical image and a second medical image. The similarity determination method comprises: dividing a target region of the first medical image into a plurality of regions; classifying each pixel of the first medical image into at least one finding; calculating a first feature amount for each finding classified in the first medical image for each of the divided regions; deriving a region similarity between the first medical image and the second medical image for each of the divided regions, on the basis of the first feature amount for each finding calculated in the first medical image and a second feature amount for each finding calculated in advance in the second medical image; and performing a weighting operation for a plurality of the region similarities with a weighting coefficient corresponding to at least one of a size of each of the divided regions or a size of a specific finding included in each of the divided regions to derive a similarity between the first medical image and the second medical image.

In addition, a non-transitory computer readable recording medium storing a program that causes a computer to perform the similarity determination method according to the present disclosure may be provided.

Another similarity determination apparatus according to the present disclosure comprises a memory that stores commands to cause a computer to perform a process of determining a similarity between a first medical image and a second medical image and a processor that is configured to execute the stored commands. The processor performs a process of: dividing a target region of the first medical image into a plurality of regions; classifying each pixel of the first medical image into at least one finding; calculating a first feature amount for each finding classified in the first medical image for each of the divided regions; deriving a region similarity between the first medical image and the second medical image for each of the divided regions, on the basis of the first feature amount for each finding calculated in the first medical image and a second feature amount for each finding calculated in advance in the second medical image; and performing a weighting operation for a plurality of the region similarities with a weighting coefficient corresponding to at least one of a size of each of the divided regions or a size of a specific finding included in each of the divided regions to derive a similarity between the first medical image and the second medical image.

According to the present disclosure, weighting is appropriately performed according to the position and distribution of findings in a target region to appropriately determine the similarity between the first medical image and the second medical image.

BRIEF DESCRIPTION OF THE DRAWINGS

FIG. 11 is a diagram illustrating an evaluation value corresponding to the type of finding for a central pixel in a certain region of interest.

FIG. 18 is a diagram illustrating weighting coefficients corresponding to region patterns.

FIG. 19 is a diagram illustrating weighting coefficients corresponding to the region patterns.

FIG. 20 is a diagram illustrating weighting coefficients corresponding to the region patterns.

DESCRIPTION OF THE PREFERRED EMBODIMENTS

Figure 1:
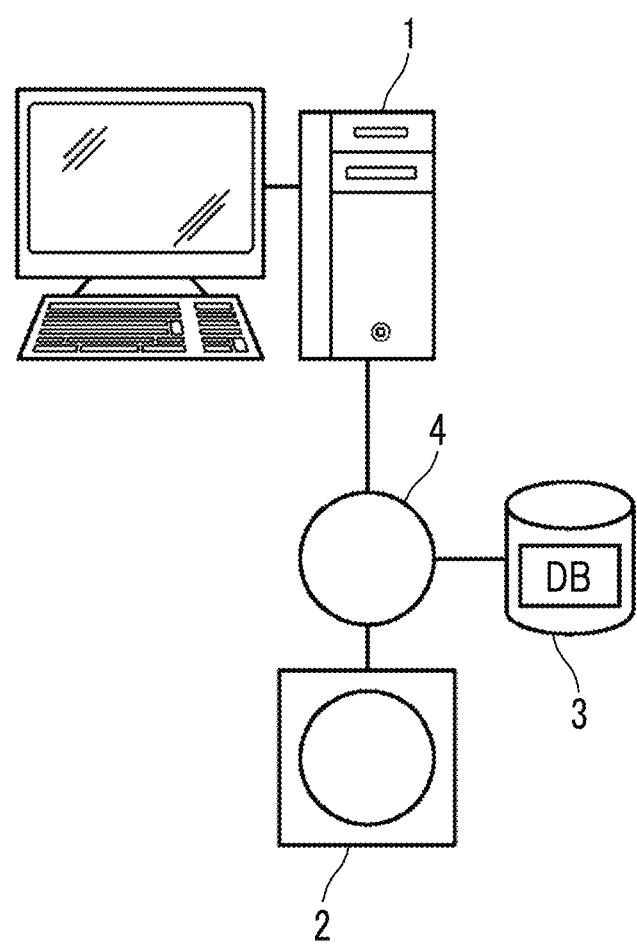
FIG. 1 is a hardware configuration diagram illustrating the outline of a diagnosis support system to which a similarity determination apparatus according to a first embodiment of the present disclosure is applied.

Hereinafter, embodiments of the present disclosure will be described with reference to the drawings. FIG. 1 is a hardware configuration diagram illustrating the outline of a diagnosis support system to which a similarity determination apparatus according to a first embodiment of the present disclosure is applied. As illustrated in FIG. 1, in the diagnosis support system, a similarity determination apparatus 1 according to this embodiment, a three-dimensional imaging apparatus 2, and an image storage server 3 are connected so as to communicate with each other through a network 4.

The three-dimensional imaging apparatus 2 is an apparatus that captures an image of a diagnosis target part of a subject to generate a three-dimensional image indicating the part and is, specifically, a CT apparatus, an MRI apparatus, a positron emission tomography (PET) apparatus, and the like. The three-dimensional image which consists of a plurality of slice images and has been generated by the three-dimensional imaging apparatus 2 is transmitted to the image storage server 3 and is then stored therein. In addition, in this embodiment, the diagnosis target part of a patient that is the subject is the lung, and the three-dimensional imaging apparatus 2 is a CT apparatus and generates a CT image of the chest including the lung of the subject as the three-dimensional image.

The image storage server 3 is a computer that stores and manages various types of data and comprises a high-capacity external storage device and database management software. The image storage server 3 performs communication with other apparatuses through the wired or wireless network 4 to transmit and receive, for example, image data. Specifically, the image storage server 3 acquires various types of data including the image data of the three-dimensional image generated by the three-dimensional imaging apparatus 2 through the network, stores the acquired data in a recording medium, such as a high-capacity external storage device, and manages the data. In addition, the storage format of the image data and the communication between the apparatuses through the network 4 are based on a protocol such as Digital Imaging and Communication in Medicine (DICOM). In this embodiment, it is assumed that the image storage server 3 stores three-dimensional images to be examined (hereinafter, referred to as examination images) and a case database DB having case images registered therein. The case database DB will be described below. In addition, in this embodiment, the examination image is a three-dimensional image consisting of one or more slice images (hereinafter, referred to as examination slice images). The case image is also a three-dimensional image consisting of one or more slice images (hereinafter, referred to as case slice images). Further, the examination image corresponds to a first medical image and the case image corresponds to a second medical image.

The similarity determination apparatus 1 is configured by installing a similarity determination program according to the present disclosure in one computer. The computer may be a workstation or a personal computer that is directly operated by a doctor who makes a diagnosis or may be a server computer that is connected to them through the network. The similarity determination program is recorded on a recording medium, such as a digital versatile disc (DVD) or a compact disc read only memory (CD-ROM), is distributed, and is installed in the computer from the recording medium. Alternatively, the similarity determination program is stored in a storage device of a server computer connected to the network, or is stored in a network storage so as to be accessed from the outside, is downloaded to the computer used by the doctor on request, and is then installed in the computer.

Figure 2:
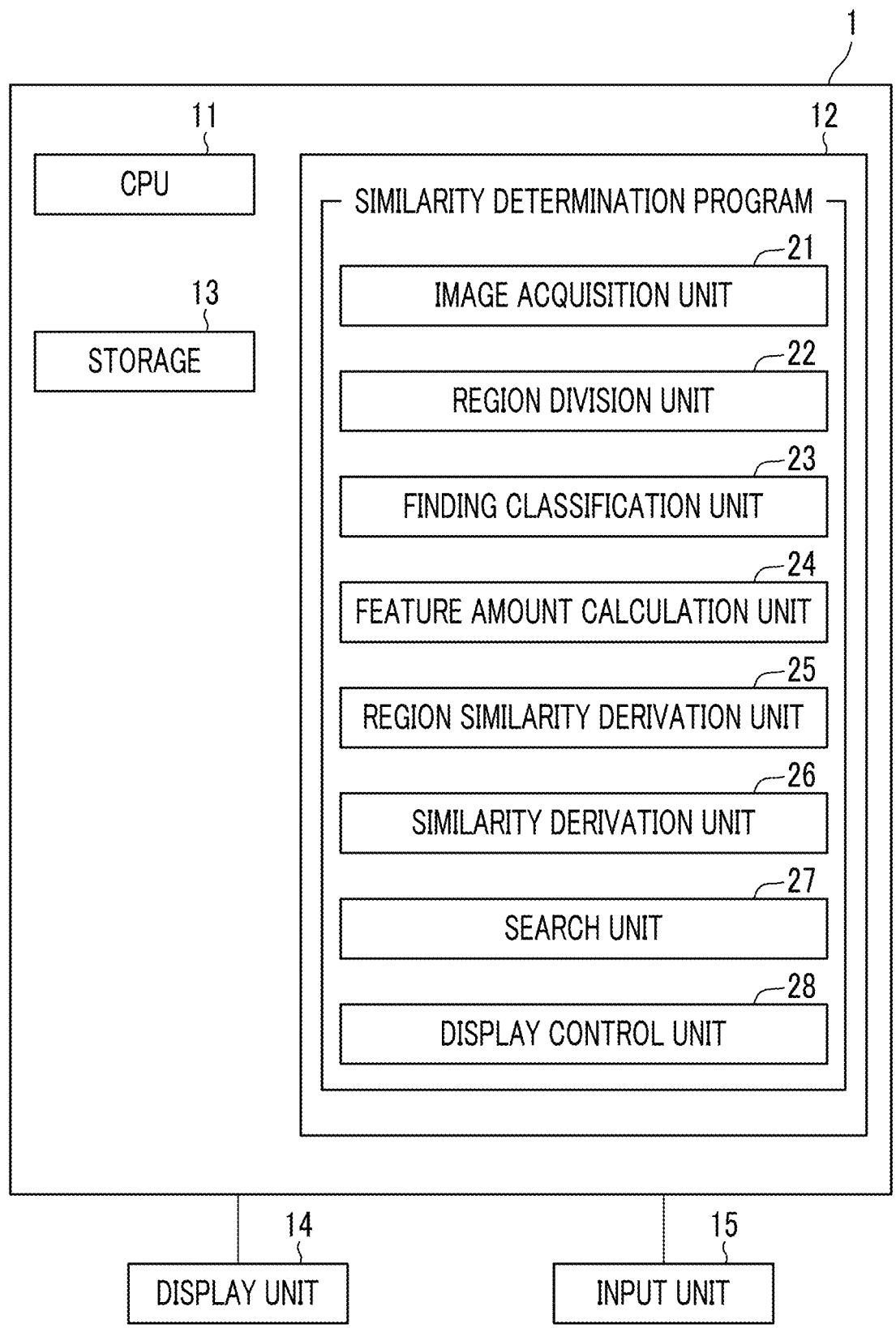
FIG. 2 is a block diagram schematically illustrating the configuration of the similarity determination apparatus according to the first embodiment.

FIG. 2 is a diagram schematically illustrating the configuration of the similarity determination apparatus according to the embodiment of the present disclosure which is implemented by installing the similarity determination program in a computer. As illustrated in FIG. 2, the similarity determination apparatus 1 has the configuration of a standard workstation and comprises a central processing unit (CPU) 11, a memory 12, and a storage 13. In addition, a display unit 14 consisting of, for example, a liquid crystal display and an input unit 15 consisting of, for example, a keyboard and a mouse are connected to the similarity determination apparatus 1.

The storage 13 consists of, for example, a hard disk drive and a solid state drive (SSD). The storage 13 stores various kinds of information which include the examination image of the subject and information required for processes and are acquired from the image storage server 3 through the network 4.

Further, the memory 12 stores the similarity determination program. The similarity determination program defines the following processes as the processes performed by the CPU 11: an image acquisition process that acquires an examination image to be examined; a region division process that divides a target region of the examination image into a plurality of regions; a finding classification process that classifies each pixel of the examination image into at least one finding; a feature amount calculation process that calculates a first feature amount for each finding classified in the examination image; a region similarity derivation process that derives a region similarity between the examination image and a case image for each divided region, on the basis of the first feature amount for each finding calculated in the examination image and a second feature amount for each finding calculated in advance in the case image; a similarity derivation process that derives a similarity between the examination image and the case image by performing a weighting operation for a plurality of region similarities with a weighting coefficient corresponding to at least one of the size of each divided region or the size of a specific finding included in each divided region; a search process that searches for a case image similar to the examination image on the basis of the derived similarity; and a display control process that displays the search results on the display unit 14.

Then, the CPU 11 performs these processes according to the program such that the computer functions as an image acquisition unit 21, a region division unit 22, a finding classification unit 23, a feature amount calculation unit 24, a region similarity derivation unit 25, a similarity derivation unit 26, a search unit 27, and a display control unit 28.

The image acquisition unit 21 acquires an examination image V0 of the subject to be examined. Further, in a case in which the examination image V0 has been stored in the storage 13, the image acquisition unit 21 may acquire the examination image V0 from the storage 13.

Figure 3:
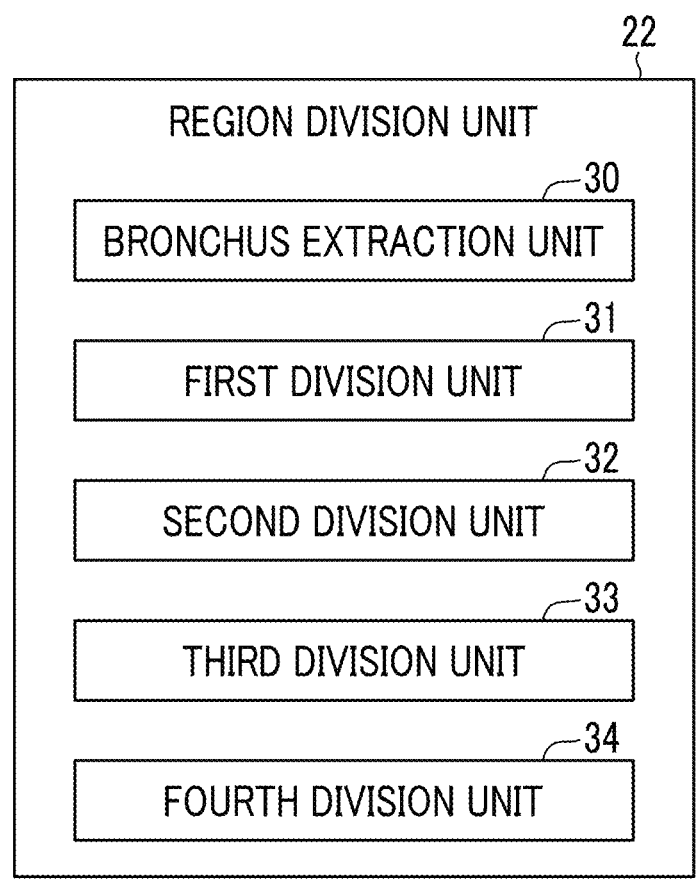
FIG. 3 is a block diagram schematically illustrating the configuration of a region division unit.

The region division unit 22 divides a lung region of the examination image into a plurality of regions. Hereinafter, the region division process will be described in detail. FIG. 3 is a block diagram schematically illustrating the configuration of the region division unit 22. As illustrated in FIG. 3, the region division unit 22 includes: a bronchus extraction unit 30 that extracts a bronchial region from the lung region of the examination image; a first division unit 31 that divides the lung region into a plurality of regions in the vertical direction on the basis of a branch position of the bronchus; a second division unit 32 that divides the lung region into a region within a specific distance from a specific branch position among a plurality of branch positions and a region other than the region within the specific distance; a third division unit 33 that divides the lung region into an outer region and an inner region; and a fourth division unit 34 that divides the lung region into a dorsal region and a ventral region.

The bronchus extraction unit 30 extracts a bronchus structure as the bronchial region from the examination image V0. Therefore, the bronchus extraction unit 30 extracts the lung region which is a target region from the examination image V0. Any method, such as a method that creates a histogram of the signal value of each pixel of the examination image V0 and performs threshold processing for the lung to extract the lung region or a region growing method based on a seed point indicating the lung, can be used as a method of extracting the lung region. In addition, a discriminator which has been subjected to machine learning so as to extract the lung region may be used.

Then, the bronchus extraction unit 30 extracts a graph structure of the bronchial region included in the lung region extracted from the examination image V0 as a three-dimensional bronchial region. As a method for extracting the bronchial region, for example, the method disclosed in JP2010-220742A can be used which extracts the graph structure of the bronchus using a Hessian matrix, classifies the extracted graph structure into a starting point, an end point, a branch point, and sides, and connects the starting point, the end point, and the branch point with the sides to extract the bronchial region. In addition, the method for extracting the bronchial region is not limited thereto.

Figure 4:
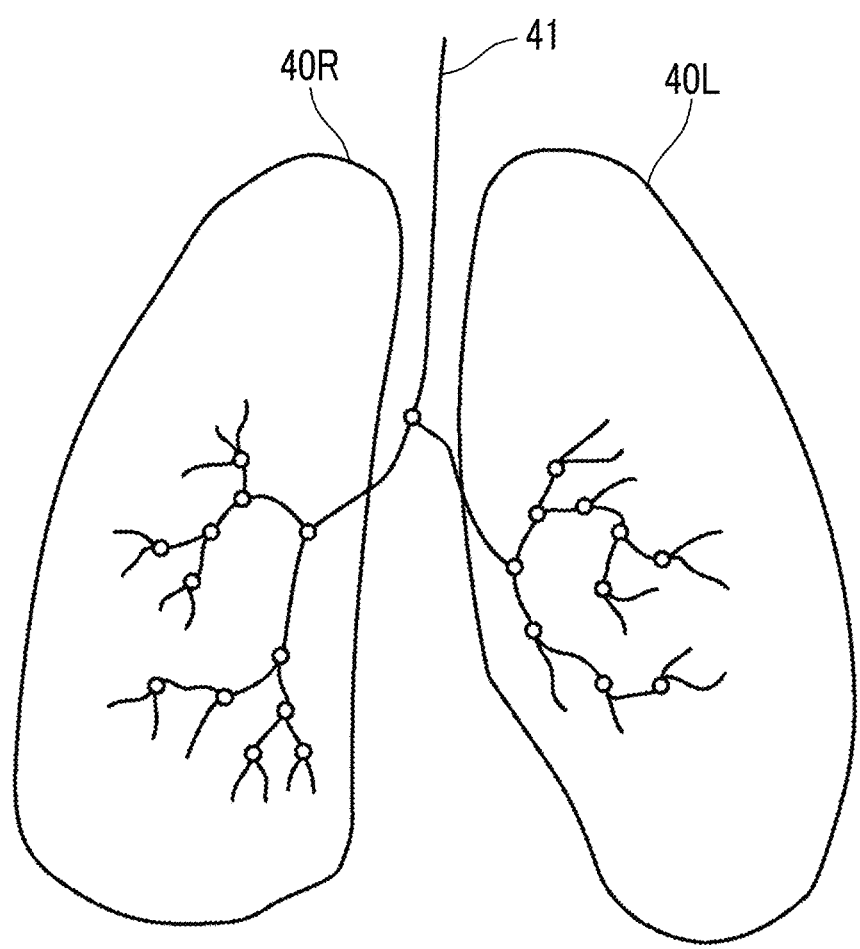
FIG. 4 is a diagram illustrating a graph structure in a bronchial region together with a lung region.

FIG. 4 is a diagram illustrating the graph structure of the bronchial region extracted by the bronchus extraction unit 30 together with the lung region. As illustrated in FIG. 4, a graph structure 41 of the bronchus is included in a left lung region 40L and a right lung region 40R. In addition, in the graph structure 41, a bronchial branch is represented by a white circle.

Here, it is diagnostically important to divide the lung region into anatomical lung segments. However, in the case in which a disease has progressed, the boundary between the lung segments is unclear. Therefore, it is difficult to divide the region on the basis of the lung segments. In this situation, in a case in which the lung region is divided into three regions with the same volume in the vertical direction, a change in the size of the region due to the expansion or contraction of a disease region is equally distributed to the divided regions. Therefore, it is difficult to understand the disease region as a characteristic of the region. Here, the bronchus included in the lung region is divided into a bronchus that extends to the upper main body and a bronchus that extends to the lower main body. Therefore, the lung region is divided on the basis of the branch position of the bronchus, which makes it easy to understand a partial change in the advanced disease in the lung region.

Figure 5:
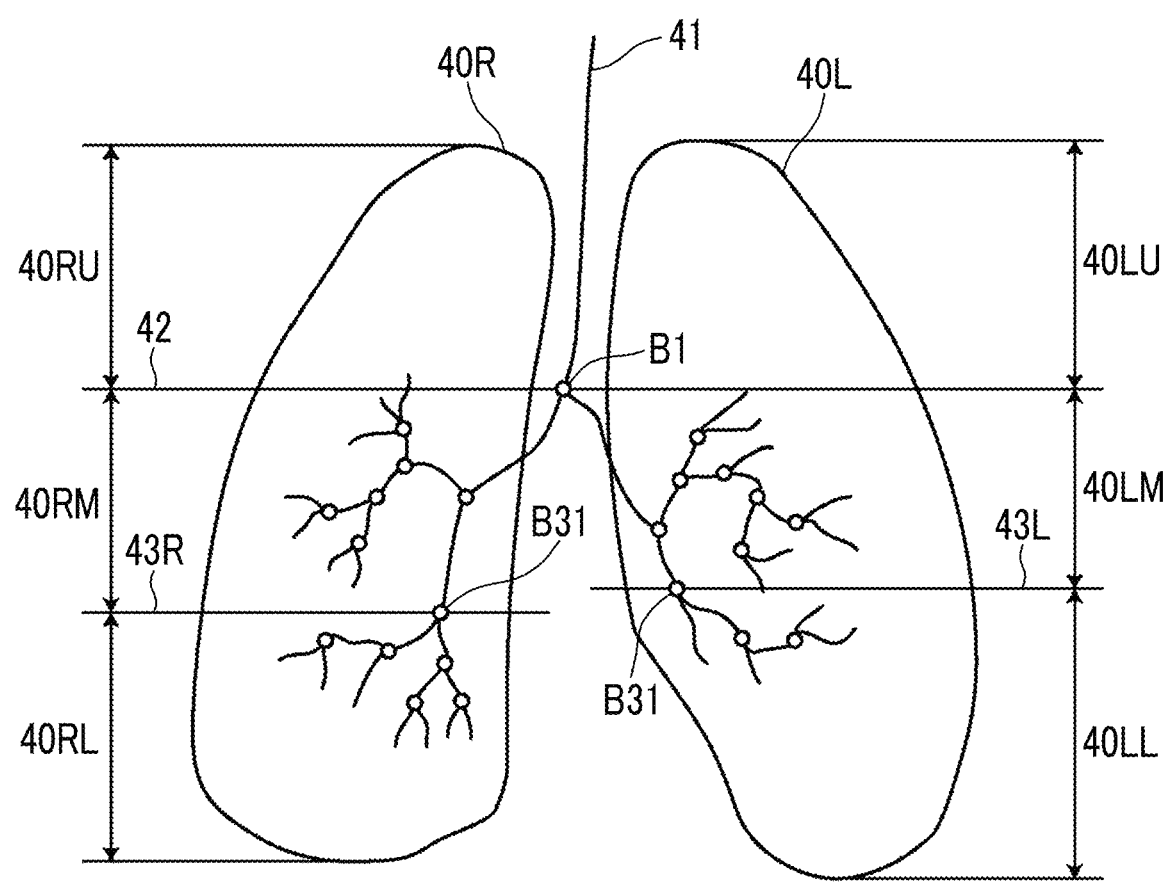
FIG. 5 is a diagram illustrating a first division process of a first division unit.

Therefore, the first division unit 31 divides the lung region into a plurality of regions in the vertical direction on the basis of the branch position of the bronchus. Specifically, each of the left and right lung regions is divided into three regions of upper, middle, and lower regions on the basis of a first bronchial branch and a third bronchial branch. In addition, the first bronchial branch in this embodiment corresponds to a branch point between the trachea and the left and right bronchi. In this embodiment, it is assumed that the branches from the first bronchial branch to the distal end of the bronchus are referred to as a second bronchial branch, a third bronchial branch, and so on. FIG. 5 is a diagram illustrating a first division process of the first division unit 31. In addition, two third bronchial branches are present in each of the left and right lung regions. It is assumed that the first division unit 31 performs region division on the basis of the third bronchial branches located on the lower side of the subject in the direction of the body axis. As illustrated in FIG. 5, the first division unit 31 sets a horizontal plane 42 in a first bronchial branch B1 and sets horizontal planes 43L and 43R in lower third bronchial branches B31 in the left and right lung regions 40L and 40R, respectively. In FIG. 5, the lung region is two-dimensionally illustrated. However, since the examination image V0 is a three-dimensional image, in practice, the horizontal planes are set as described above. Here, the horizontal plane means a plane perpendicular to the body axis of the subject whose examination image V0 has been acquired.

The first division unit 31 divides the left lung region 40L into three regions of a left upper lung region 40LU between the horizontal plane 42 and the upper end of the left lung region 40L, a left middle lung region 40LM between the horizontal plane 42 and the horizontal plane 43L, and a left lower lung region 40LL between the horizontal plane 43L and the lower end of the left lung region 40L. In addition, the first division unit 31 divides the right lung region 40R into three regions of a right upper lung region 40RU between the horizontal plane 42 and the upper end of the right lung region 40R, a right middle lung region 40RM between the horizontal plane 42 and the horizontal plane 43R, and a right lower lung region 40RL between the horizontal plane 43R and the lower end of the right lung region 40R.

In addition, large bronchi and blood vessels are present in a central region of the lung in the vicinity of a hilar region. Therefore, in a case in which the similarity between the examination image V0 and the case image is determined, it is preferable to distinguish the central region from other regions which are mainly composed of alveoli. In the central region of the lung, it is also preferable to use the branch point of the bronchus as a reference point since the overall lung shrinkage and positional deviation occur due to the disease.

Figure 6:
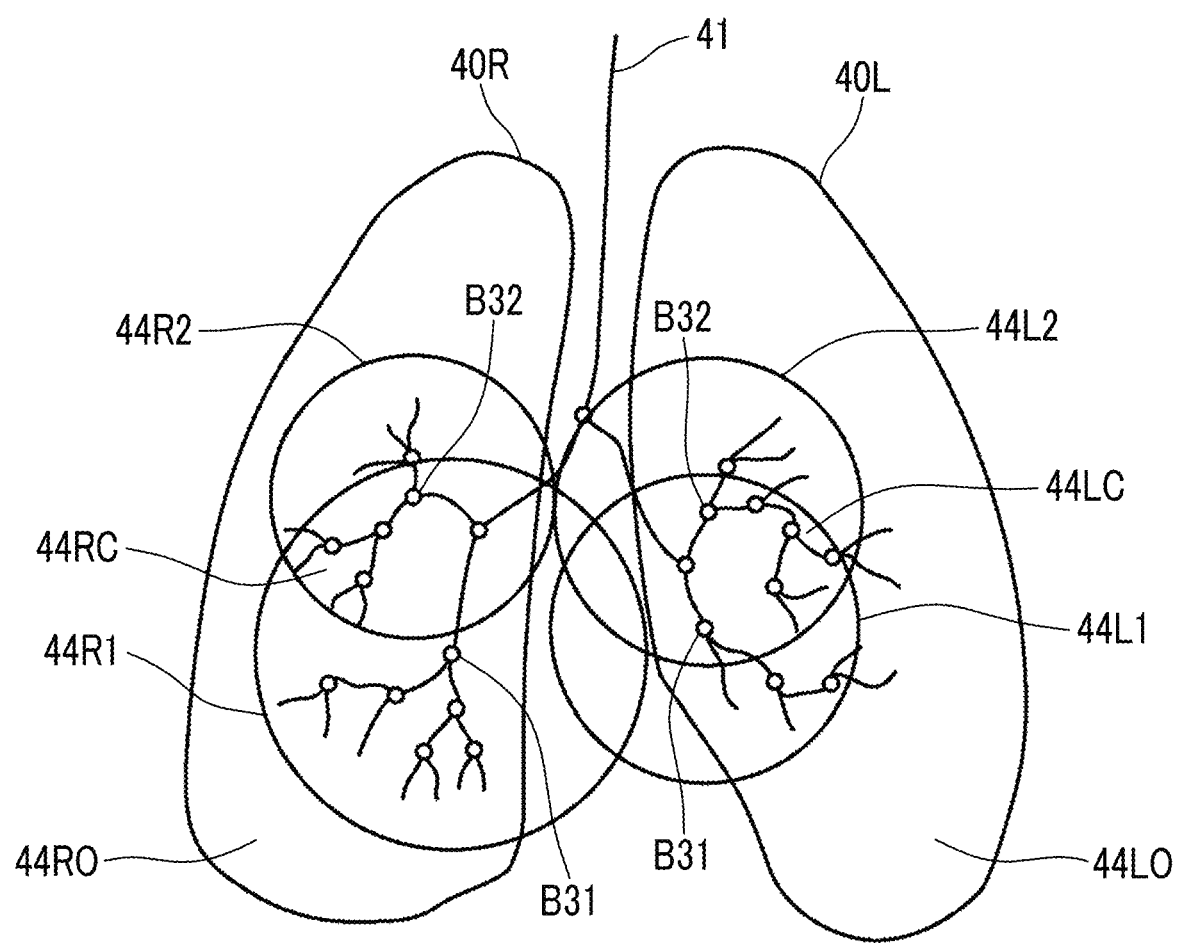
FIG. 6 is a diagram illustrating a second division process of a second division unit.

The second division unit 32 divides the lung region into a region within a specific distance from a specific branch position among a plurality of branch positions and a region other than the region within the specific distance. Specifically, in the left and right lung regions 40L and 40R, a spherical region having a specific radius centered on the third bronchial branch is set. FIG. 6 is a diagram illustrating a second division process of the second division unit 32. In addition, two third bronchial branches are present in each of the left and right lung regions. The second division unit 32 sets a spherical region having a specific radius in each of two third bronchial branches B31 and B32 in the left and right lung regions 40L and 40R. That is, as illustrated in FIG. 6, the second division unit 32 sets a spherical region 44L1 centered on the lower third bronchial branch B31 and a spherical region 44L2 centered on the upper third bronchial branch B32 in the left lung region 40L. In addition, the second division unit 32 sets a spherical region 44R1 centered on the lower third bronchial branch B31 and a spherical region 44R2 centered on the upper third bronchial branch B32 in the right lung region 40R.

Further, the radius of the spherical region may be set according to the distance from the third bronchial branches B31 and B32 to the left and right ends of the left and right lung regions. For example, the radius of the spherical region may be set to 0.5 to 0.65 times the distance. Here, in the right lung region 40R illustrated in FIG. 6, the distance from the third bronchial branch B31 to the right end of the right lung region 40R is longer than the distance from the third bronchial branch B32 to the right end of the right lung region 40R. Therefore, the radius of the spherical region 44R1 is larger than the radius of the spherical region 44R2. In contrast, in the left lung region 40L illustrated in FIG. 6, the distances from the third bronchial branches B31 and B32 to the left end of the left lung region 40L are substantially equal to each other. Therefore, the radius of the spherical region 44L1 is substantially equal to the radius of the spherical region 44L2.

Then, the second division unit 32 divides the left lung region 40L into a left central region 44LC that consists of the spherical region 44L1 and the spherical region 44L2 and a region 44LO other than the left central region 44LC. Further, the second division unit 32 divides the right lung region 40R into a right central region 44RC that consists of the spherical region 44R1 and the spherical region 44R2 and a region 44RO other than the right central region 44RC. In addition, the regions 44LO and 44RO are regions that are mainly composed of alveoli.

Figure 7:
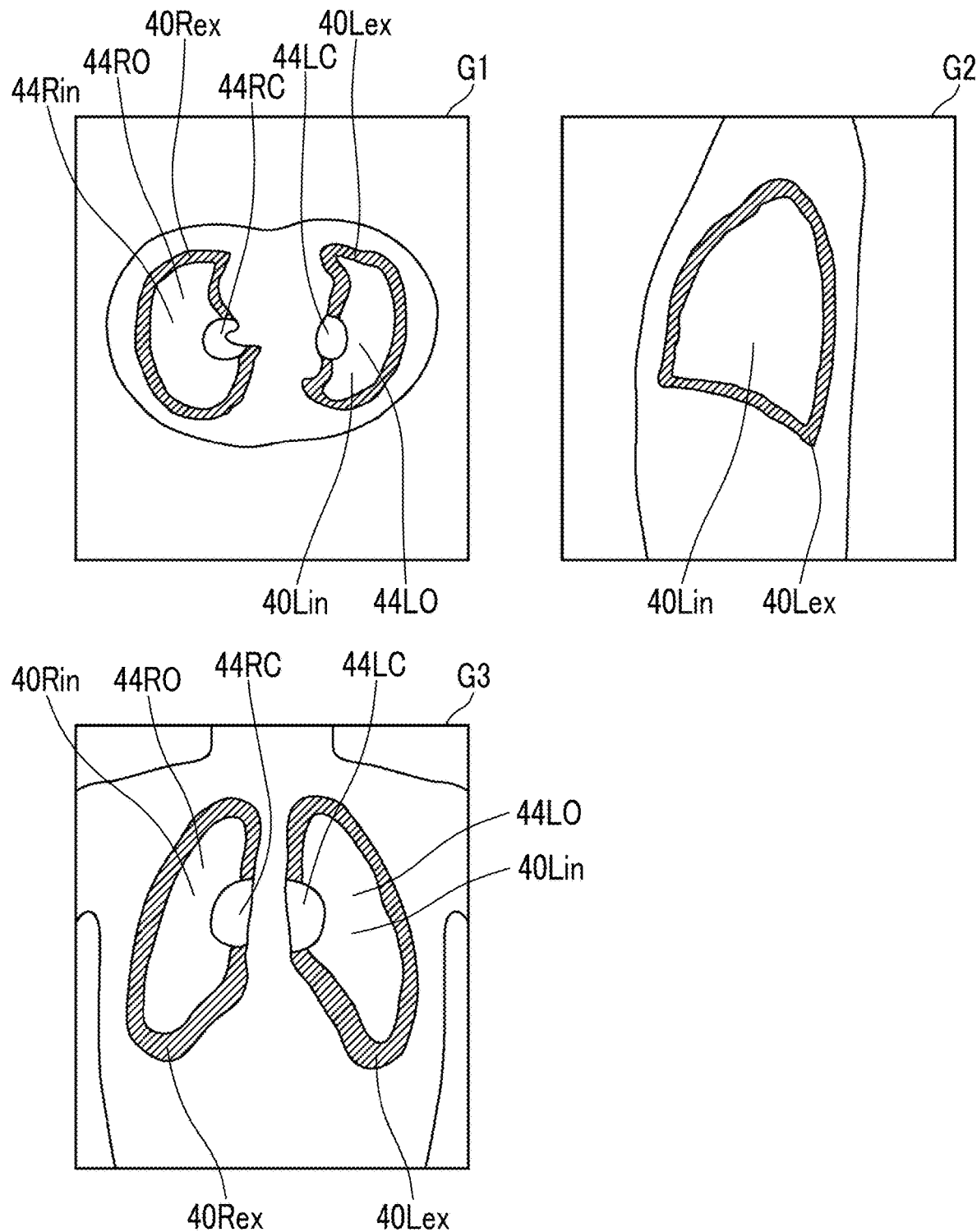
FIG. 7 is a diagram illustrating a third division process of a third division unit.

The third division unit 33 divides the lung region into an outer region and an inner region. Here, the third division unit 33 divides only the region 44LO and the region 44RO divided by the second division unit 32 into the outer region and the inner region. FIG. 7 is a diagram illustrating a third division process of the third division unit 33. In addition, FIG. 7 illustrates a tomographic image G1 of the axial plane, a tomographic image G2 of the sagittal plane, and a tomographic image G3 of the coronal plane. The third division unit 33 divides the lung region into an outer region having a volume that is 50 to 60% of the volume of the lung region from the pleura and an inner region other than the outer region. Specifically, the third division unit 33 divides the left lung region 40L into an outer region 40Lex and an inner region 40Lin and divides the right lung region 40R into an outer region 40Rex and an inner region 40Rin.

In addition, the third division unit 33 divides each of the left upper lung region 40LU, the left middle lung region 40LM, the left lower lung region 40LL, the right upper lung region 40RU, the right middle lung region 40RM, and the right lower lung region 40RL divided by the first division unit 31 into an outer region and an inner region.

Figure 8:
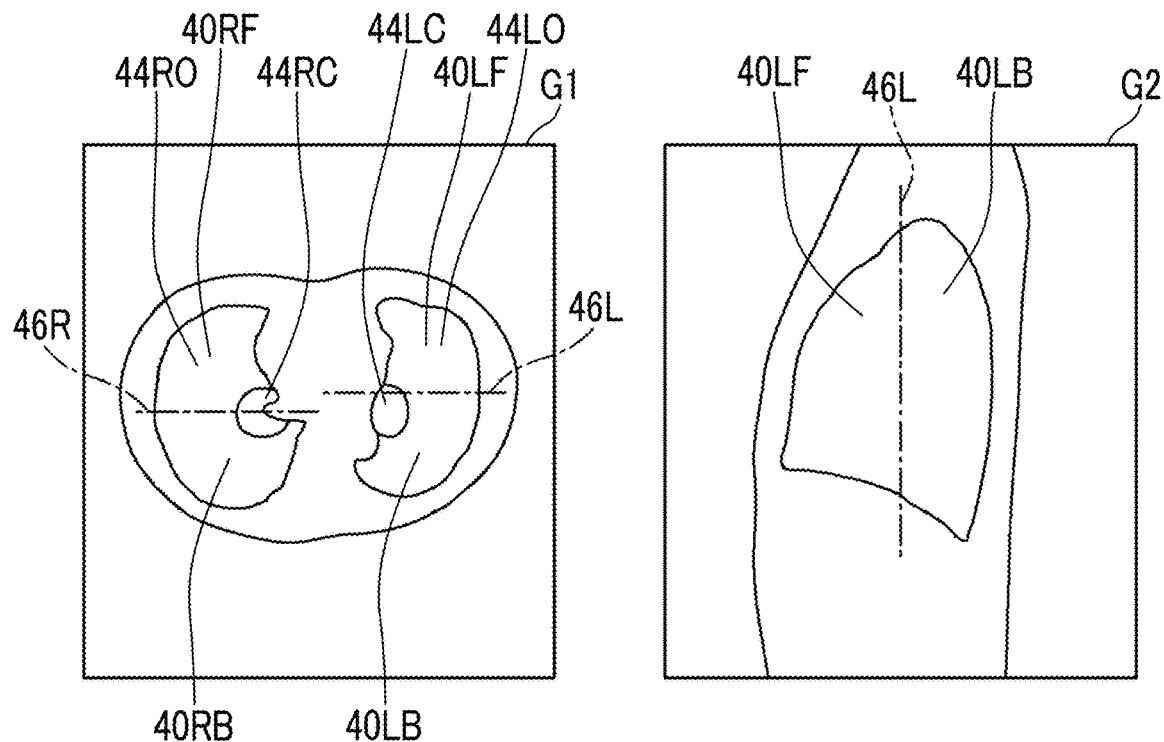
FIG. 8 is a diagram illustrating a fourth division process of a fourth division unit.

The fourth division unit 34 divides the lung region into a dorsal region and a ventral region. Here, the fourth division unit 34 divides only the region 44LO and the region 44RO divided by the second division unit 32 into a dorsal region and a ventral region. FIG. 8 is a diagram illustrating a fourth division process of the fourth division unit 34. In addition, FIG. 8 illustrates the tomographic image G1 of the axial plane and the tomographic image G2 of the sagittal plane. The fourth division unit 34 divides the lung region into the dorsal region and the ventral region on the basis of the coronal plane which divides the volume of the lung region into two equal parts. Specifically, the fourth division unit 34 sets a coronal cross section 46L as a reference in the left lung region 40L and divides the left lung region 40L into a dorsal region 40LB and a ventral region 40LF on the basis of the coronal cross section 46L. Further, the fourth division unit 34 sets a coronal cross section 46R as a reference in the right lung region 40R and divides the right lung region 40R into a dorsal region 40RB and a ventral region 40RF on the basis of the coronal cross section 46R.

The fourth division unit 34 further divides the outer region and the inner region of each of the left upper lung region 40LU, the left middle lung region 40LM, the left lower lung region 40LL, the right upper lung region 40RU, the right middle lung region 40RM, and the right lower lung region 40RL divided by the third division unit 33 into a dorsal region and a ventral region.

Figure 9:
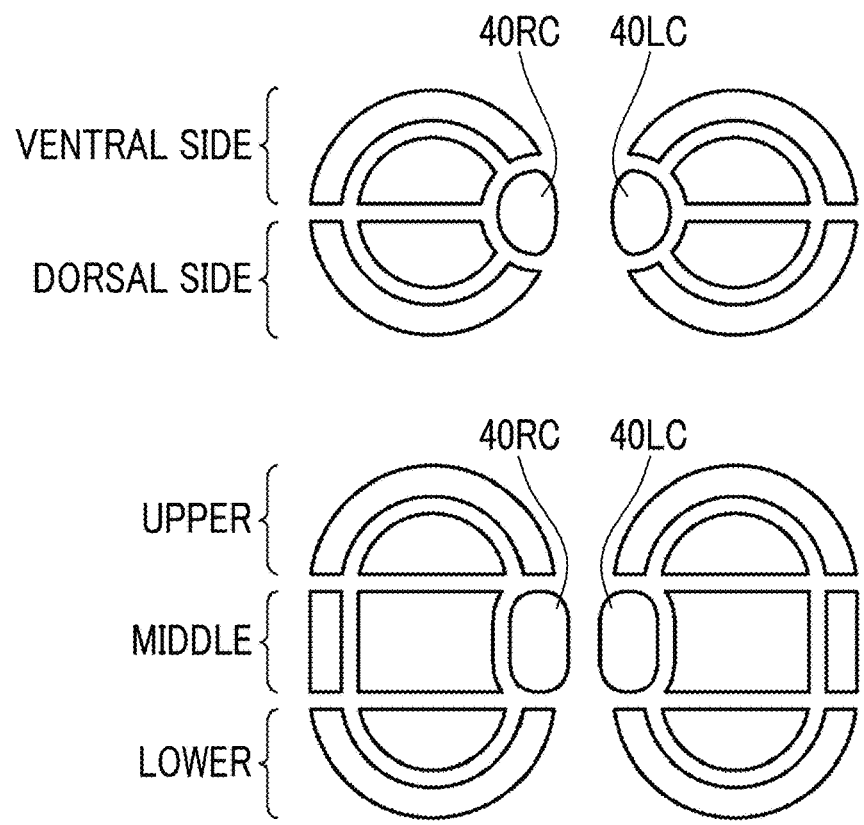
FIG. 9 is a diagram schematically illustrating division results of the lung region by the first to fourth division units.

FIG. 9 is a diagram schematically illustrating the division results of the lung region by the first to fourth division units 31 to 34. In FIG. 9, the axial cross section of the lung region is not closed in an upper diagram and the coronal cross section is not illustrated in a lower diagram. Further, in FIG. 9, reference numerals are given to only a left central region 40LC and a right central region 40RC, and the reference numerals of the other regions obtained by the division are omitted. Each of the left and right lung regions is divided into 13 regions by the division by the first to fourth division units 31 to 34.

In addition, the division of the lung region by the region division unit 22 is not limited to the first to fourth division processes. For example, in interstitial pneumonia which is one of the diseases of the lung, lesion sites may spread around the bronchi and the blood vessels. Therefore, the bronchial region and the blood vessel region may be extracted in the lung region, and the lung region may be divided into a region in a predetermined range around the bronchial region and the blood vessel region and the other regions. In addition, the predetermined range may be a region in the range of about 1 cm from the surfaces of the bronchus and the blood vessel.

The finding classification unit 23 classifies each pixel of the lung region included in the examination image V0 into at least one finding. Specifically, the finding classification unit 23 calculates a plurality of evaluation values indicating the possibility that each pixel of the lung region included in the examination image V0 will be each of a plurality of types of tissues or lesions (for example, findings) and classifies each pixel of the examination image V0 into at least one of the plurality of types of findings on the basis of the plurality of evaluation values. In this embodiment, it is assumed that the finding classification unit 23 classifies each pixel of the examination image V0 into one finding.

The finding classification unit 23 according to this embodiment includes a discriminator which consists of a multi-layer neural network generated by deep learning that is one kind of machine learning and specifies the type of finding, to which each pixel of the examination image V0 belongs, using the discriminator. In addition, the machine learning method is not limited to deep learning, and other methods including a support vector machine may be used.

In each layer of the multi-layer neural network, arithmetic processing is performed for data of a plurality of different feature amounts obtained by the previous layer, using various kernels. Then, in the subsequent layers, arithmetic processing can be further performed for the data of the feature amounts obtained by the arithmetic processing to improve the recognition rate of the feature amounts, and the input data can be classified into a plurality of classes.

Further, in this embodiment, the multi-layer neural network receives the examination image V0 as an input and outputs the classification result of the lung region into a plurality of types of findings. However, the multi-layer neural network may be configured such that it receives each of a plurality of examination slice images forming the examination image V0 as an input and outputs the classification result of the lung region into a plurality of types of findings.

Figure 10:
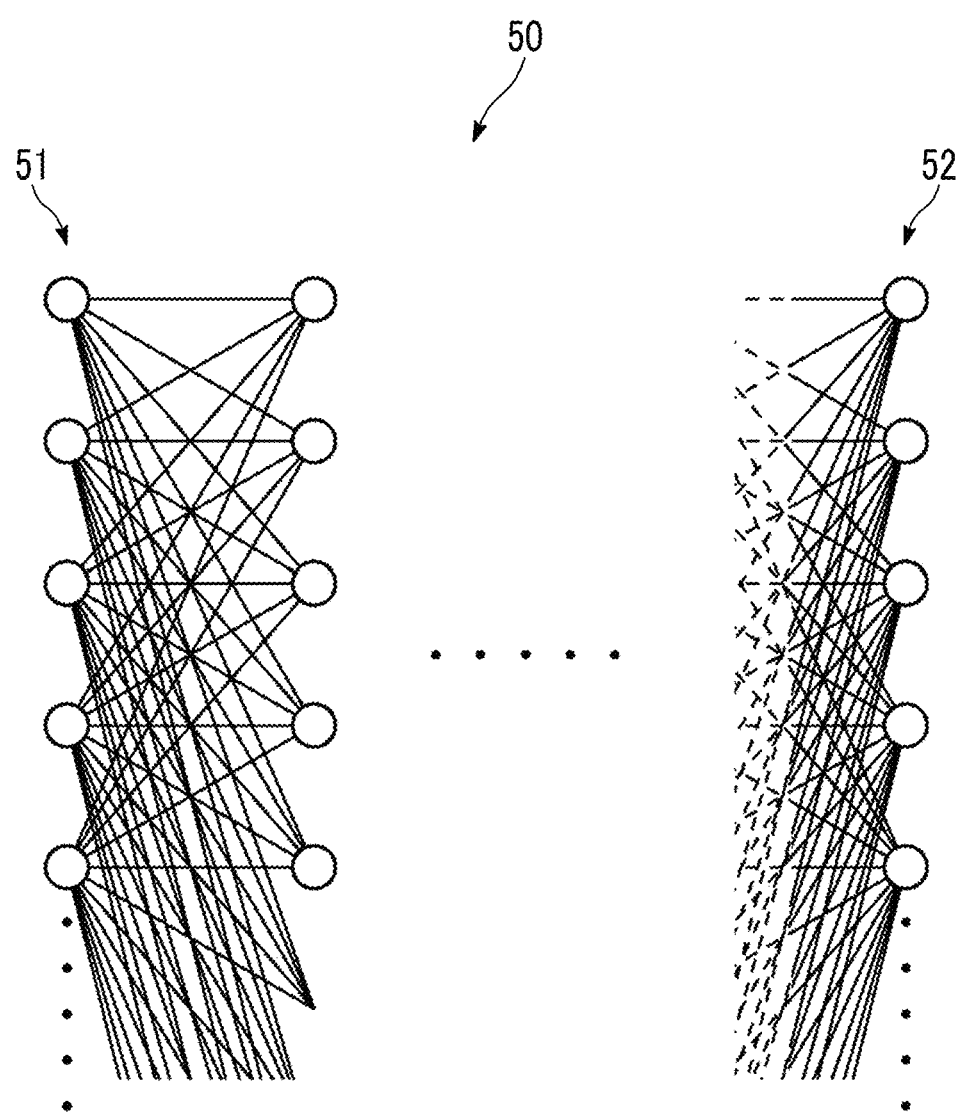
FIG. 10 is a diagram illustrating an example of a multi-layer neural network.

FIG. 10 is a diagram illustrating an example of the multi-layer neural network. As illustrated in FIG. 10, a multi-layer neural network 50 consists of a plurality of layers including an input layer 51 and an output layer 52. In this embodiment, learning is performed such that the lung region included in the examination image V0 is classified into a plurality of findings, such as an infiltrative shadow, a mass shadow, a ground-glass shadow, a centrilobular nodular shadow, a non-centrilobular nodular shadow, a punctate shadow, a reticular shadow, a linear shadow, interlobular septal thickening, a honeycomb lung, a cyst, a low absorption area (emphysema), emphysema tendency, a cavity, pleural thickening, pleural effusion, bronchodilatation, traction bronchiectasis, a blood vessel, a normal lung, a chest wall, and mediastinum. In addition, the types of findings are not limited thereto and may be more or less than these findings.

In this embodiment, the multi-layer neural network 50 learns these findings using a large amount of training data such as millions of training data items. In the learning, a region of interest with a predetermined size (for example, 1.5 cm×1.5 cm) is cut out from a tomographic image in which the types of findings have been known. Then, the region of interest is used as the training data. Then, the training data is input to the multi-layer neural network 50 and the result of a finding type classification process (hereinafter, referred to as a classification result) is output from the multi-layer neural network 50. Then, the output result is compared with the training data, and the weight of the connection between the layers of units (represented by circles in FIG. 10) included in each layer of the multi-layer neural network 50 is corrected from the output side to the input side according to whether the answer is correct or incorrect. The correction of the weight of the connection is repeated using a large amount of training data a predetermined number of times or until the accuracy rate of the output classification result reaches 100%, and the learning ends.

Further, in a case in which the input image is an examination slice image, in the learning of the multi-layer neural network 50, a two-dimensional region normalized to a predetermined size (for example, 1.5 cm×1.5 cm) is cut out from a slice image forming a three-dimensional image in which a lesion has been known, and the image of the cut-out two-dimensional region is used as the training data.

The finding classification unit 23 extracts a lung region that is a target region from the examination image V0 for classification. The lung region may be extracted by the same method as in the bronchus extraction unit 30. In addition, the finding classification unit 23 may use the lung region extracted by the bronchus extraction unit 30.

In a case in which the finding classification process is performed, the finding classification unit 23 sequentially cuts out the region of interest having the same size as the training data from the lung region of the examination image V0 and inputs the region of interest to the discriminator consisting of the multi-layer neural network 50. Then, for a central pixel of the cut-out region of interest, an evaluation value corresponding to each classification of the findings is output. In addition, the evaluation value corresponding to each classification is an evaluation value indicating the possibility that the central pixel will belong to each classification. As the evaluation value becomes larger, the possibility that the central pixel will belong to the classification becomes higher.

FIG. 11 is a diagram illustrating an evaluation value corresponding to the type of finding for a central pixel of a certain region of interest. In FIG. 11, evaluation values for some findings are illustrated for simplicity of description. In this embodiment, the discriminator classifies the central pixel of the region of interest into a finding with the maximum evaluation value among a plurality of findings. For example, in a case in which the evaluation values illustrated in FIG. 11 are acquired, the central pixel of the region of interest has the highest possibility of being the reticular shadow and has the second highest possibility of being the ground-glass shadow. On the contrary, there is almost no possibility that the central pixel will be the normal lung or the low absorption area. Therefore, in a case in which the evaluation values as illustrated in FIG. 11 are acquired, the central pixel of the region of interest is classified into the reticular shadow having a maximum evaluation value of 8.5 by the finding classification process. In this way, all of the pixels of the lung region included in the examination image V0 are classified into any of a plurality of types of findings.

In accordance with the above, the finding classification unit 23 classifies the central pixel of the region input to the multi-layer neural network 50 into a finding with the maximum evaluation value among the plurality of evaluation values and generates the classification result of findings. In this way, all of the pixels of the lung region included in the examination image V0 are classified into any of a plurality of types of findings.

Figure 12:
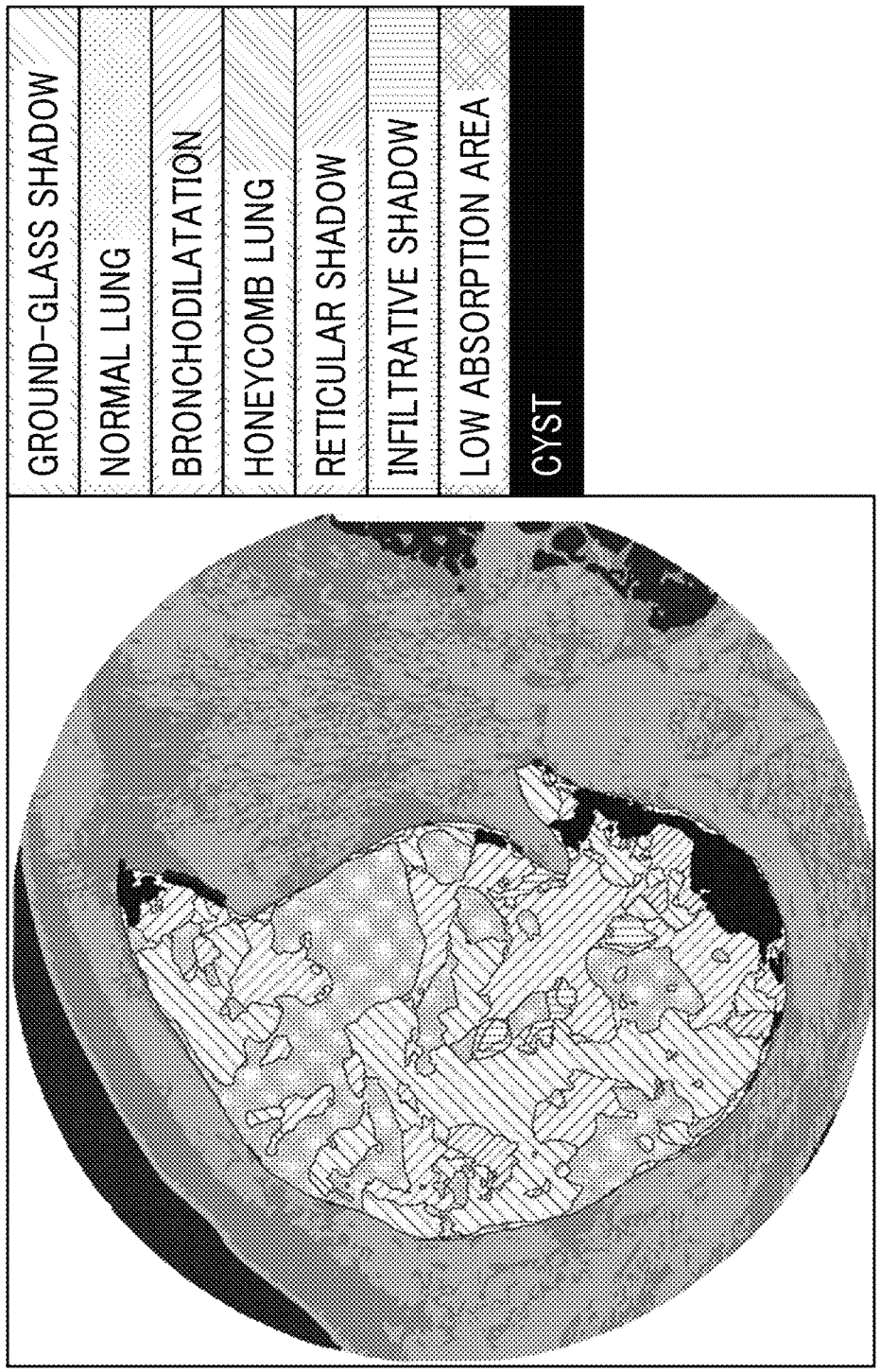
FIG. 12 is a diagram illustrating a cross section of a mapping image to which colors corresponding to classifications are assigned.

The finding classification unit 23 assigns a color to each classified region of the examination image V0 on the basis of the result of the finding classification process to generate a mapping image. Specifically, the finding classification unit 23 assigns the same color to the pixels classified into the same finding for all of the pixels in a three-dimensional space classified into any of the plurality of types of findings to generate a three-dimensional mapping image. FIG. 12 is a diagram illustrating a cross section of the mapping image in which colors corresponding to a plurality of types of classifications are assigned. In addition, FIG. 12 illustrates the mapping image in a case in which the pixels are classified into eight types of findings, that is, a ground-glass shadow, a normal lung, bronchodilatation, a honeycomb lung, a reticular shadow, an infiltrative shadow, a low absorption area, and a cyst for simplicity of description. In addition, the display control unit 28 which will be described below may display the mapping image on the display unit 14. In a case in which the mapping image is displayed on the display unit 14, as illustrated in FIG. 12, a tomographic image of any cross section in the three-dimensional mapping image may be displayed. However, the present disclosure is not limited thereto, and the three-dimensional mapping image may be displayed on the display unit 14.

The feature amount calculation unit 24 calculates a feature amount for each of the classified findings in the examination image V0. Specifically, the feature amount calculation unit 24 calculates, as the feature amount, at least one of the size of a region for each finding, average density for each finding, the variance of density for each finding, the number of regions for each finding, or the average size of the region for each finding. In addition, it is assumed that the feature amount calculated for the examination image V0 is referred to as a first feature amount. Further, for example, the size of the region for each finding, the number of regions for each finding, and the average size of the region for each finding are size feature amounts. The volume of the region for each finding can be used as the size of the region for each finding.

In addition, a file name, evaluation values for a plurality of findings in each pixel, and feature amounts for each finding are registered for each of a plurality of case images in the above-described case database DB. It is assumed that the feature amount registered in the case database DB for the case image is referred to as a second feature amount. The first feature amount and the second feature amount are normalized to values that are equal to or greater than 0 and equal to or less than 1. In a case in which evaluation values for a plurality of findings in each pixel and feature amounts for each finding are acquired for the examination image V0, the examination image V0 is registered as a new case image in the case database DB. In this case, the evaluation value and the first feature amount for the examination image V0 are registered as the evaluation value and the second feature amount for the new case image in the case database DB.

The region similarity derivation unit 25 derives a region similarity which is a similarity between the examination image V0 and the case image for each divided region on the basis of the first feature amount for each finding calculated in the examination image V0 and the second feature amount for each finding calculated in advance in the case image. In addition, the region similarity derivation unit 25 derives the region similarity for each of the corresponding regions of the examination image V0 and all of the case images registered in the case database DB.

Therefore, the region similarity derivation unit 25 normalizes the first feature amount calculated for the examination image V0 to a value that is equal to or greater than 0 and equal to or less than 1. Then, the region similarity derivation unit 25 calculates, as a feature amount difference Ddi, a difference in the distance between the first feature amount and the second feature amount of the case image for each finding in each divided region, as represented by the following Expression (1). Further, in Expression (1), i indicates the type of finding, k indicates the type of feature amount, Tvk indicates the first feature amount for each type in the examination image V0, and Tck indicates the second feature amount for each type in the case image. Furthermore, the first feature amount and the second feature amount whose difference is calculated are the same type. In addition, in Expression (1), $\Sigma$ indicates the calculation of the sum of $(Tvk-Tck)^2$ for each type of feature amount. Further, since the first feature amount and the second feature amount are normalized to a value that is equal to or greater than 0 and equal to or less than 1, the feature amount difference Ddi is also a value that is equal to or greater than 0 and equal to or less than 1. Furthermore, in a case in which the first feature amount Tvk is equal to the second feature amount Tck, the feature amount difference Ddi is 0. Moreover, instead of the difference in the distance between the first feature amount and the second feature amount, for example, the absolute value of the difference between the first feature amount and the second feature amount may be used.

$$Ddi = \sqrt{(\Sigma(Tvk-Tck)^2)} \quad (1)$$

Then, the region similarity derivation unit 25 calculates a region similarity Sj0 between the examination image V0 and the case image using the following Expression (2). That is, in each of the divided regions, the feature amount differences Ddi for each finding are added for all of the findings to calculate the region similarity Sj0. In Expression (2), j indicates the type of the divided region. Further, in a case in which the region similarity Sj0 is calculated using Expression (2), the similarity between the corresponding regions of the examination image V0 and the case image becomes higher as the distance between the first feature amount and the second feature amount becomes shorter. Therefore, a negative sign is given to Expression (2) such that, as the similarity between the examination image V0 and the case image becomes higher, the value of the region similarity Sj0 becomes larger.

$$Sj0 = -\Sigma Ddi \quad (2)$$

In contrast, in the calculation of the region similarity Sj0 by the above-mentioned Expression (2), in a case in which the same findings have the same size, the region similarity Sj0 is 0. However, in a case in which the same lesions are compared with each other, the fact is that as the size of the lesions becomes larger, the similarity between the lesions becomes higher. In a case in which the region similarity Sj0 is calculated by the above-mentioned Expression (2), there is no difference between a case in which findings having a relatively large size have the same feature amount and a case in which findings having a relatively small size have the same feature amount, and it is difficult to reflect the fact that, as the size of the lesions becomes larger, the similarity between the lesions becomes higher.

For this reason, for the same finding included in the divided regions of the examination image V0 and the case image, only the difference in size therebetween is not treated and it is preferable that the region similarity becomes higher as the sizes become more similar to each other. Therefore, in this embodiment, the region similarity derivation unit 25 further calculates a difference Dsi between the sizes of the findings in each divided region of the examination image V0 and the case image, using the following Expression (3). Further, in Expression (3), Pvi in each divided region indicates the finding occupancy of a finding i in the examination image V0, and Pci indicates the finding occupancy of the finding i in the case image.

$$Dsi = 1 - |Pvi - Pci|\Sigma(Pvi + Pci) \quad (3)$$

Therefore, it is preferable that the region similarity derivation unit 25 calculates a region similarity Sj1 between the examination image V0 and the case image using the following Expression (4). Here, Ddi is a value that becomes larger as the similarity between the feature amounts of the findings in each divided region of the examination image V0 and the case image becomes higher, and Dsi is a value that becomes larger as the sizes of the findings in each divided region of the examination image V0 and the case image become more similar to each other. Therefore, it is possible to calculate the region similarity Sj1 that becomes higher as the corresponding regions of the examination image V0 and the case image become more similar to each other with Expression (4) by considering the sizes of the same findings.

$$Sj1 = \Sigma(Dsi \cdot Ddi) \quad (4)$$

Figures 13, 14:
FIG. 13 is a diagram illustrating calculation results of the volumes of findings.
FIG. 14 is a diagram illustrating a search result list.

Here, the finding occupancy is calculated as follows. First, the region similarity derivation unit 25 calculates the volume of each finding i in each divided region. Here, the volume of the finding can be calculated by multiplying the number of pixels of each finding included in each region by the volume per voxel in the examination image V0. FIG. 13 illustrates the calculation results of the volume of the findings. In FIG. 13, the unit of volume is cubic millimeters. Then, the region similarity derivation unit 25 normalizes the volume of the finding with the volume of each region to calculate the finding occupancy (=the volume of the finding/the volume of the lung). In addition, the finding occupancy may be included as the size feature amount in the first feature amount and may be calculated by the feature amount calculation unit 24.

Further, in a case in which the region similarity Sj1 is calculated by Expression (4), the maximum value of the region similarity Sj1 varies depending on each divided region of the examination image V0. Therefore, it is preferable to normalize the region similarity Sj1 under the condition that the region similarity Sj1 between the corresponding regions of the examination image V0 and the case image is the maximum value, that is, the condition that there is no difference between the corresponding regions of the examination image V0 and the case image. Expression (5) is obtained by normalizing the region similarity Sj1 calculated by Expression (4) under the condition Sjmax that the region similarity Sj1 between the corresponding regions of the examination image V0 and the case image is the maximum value. In Expression (5), Sj2 indicates the normalized region similarity.

$$Sj2 = Sj1/Sj \max = \Sigma(Dsi - Ddi)/Sj \max \quad (5)$$

In addition, in a case in which the region similarity is calculated by Expression (2), it is also preferable to normalize the region similarity Sj0. Expression (6) is obtained by normalizing Expression (2) under the condition that the region similarity Sj0 between the corresponding regions of the examination image V0 and the case image is the maximum value. In Expression (6), Sj3 indicates the normalized region similarity.

$$Sj3 = Sj0/Sj \max = \Sigma Dsi/Sj \max \quad (6)$$

The similarity derivation unit 26 performs a weighting operation for a plurality of region similarities on the basis of a weighting coefficient corresponding to at least one of the size of each divided region or the size of a specific finding included in each divided region to derive the similarity between the examination image V0 and the case image. In addition, it is assumed that the similarity derivation unit 26 derives the similarity between the examination image V0 and the case image using the region similarity Sj2.

Here, in pulmonary fibrosis and the like in lung diseases, reticular shadows and honeycomb lung findings are likely to occur predominantly in the subpulmonary and subpleural regions. Conversely, the initial stage of general bacterial pneumonia does not occur just below the pleura and ground-glass shadows and infiltrative shadows develop from the inside. Further, for example, aspiration pneumonia is likely to occur on the dorsal side of the lung. In accordance with the above, for the lung diseases, each disease has a characteristic onset position in the lung. In order to derive the similarity between the examination image V0 and the case image in consideration of the features of the onset position, the region similarities Sj2 derived for all of the divided regions can be added to derive the similarity between the examination image V0 and the case image in consideration of the similarity between the onset positions of the diseases.

However, the size of the region divided by the region division unit 22 as described above varies depending on the region. The region similarity Sj2 may be weighted by the size of the divided region in order to derive the similarity without depending on the size of the region. Further, for example, there are medically important regions and it is preferable to increase the weight for the important region.

Furthermore, in general, there is a technique that derives the similarity mainly using lesions and searches for a case image. Therefore, a region in which a lesion is present is the important region, and the size of the lesion in each divided region of the examination image V0 is normalized with the sizes of the lesions in the entire region of the lung. Then, weighting corresponding to the lesion ratio acquired by the normalization is performed for the region similarity Sj2 to derive the similarity between the examination image V0 and the case image with emphasis on the lesion. Further, the derivation of the similarity enables the doctor to search for a desired case image.

For example, it is assumed that the lung region is divided into 10 regions. It is assumed that, among the 10 divided regions, nine regions are in a normal state and a lesion is present in one region. In a case in which all of the region similarities derived in each of the 10 regions are 0.9 and all of the regions are equally evaluated, the similarity between the examination image V0 and the case image is 9.0. In contrast, in a case in which all of the region similarities derived in the nine regions in the normal state among the 10 regions are 1.0, the region similarity derived in the region in which the lesion is present is 0, and all of the regions are equally evaluated, the similarity between the examination image V0 and the case image is 9.0, which is the same as in the case in which all of the region similarities derived in each of the 10 regions are 0.9. Therefore, it is possible to derive the similarity in consideration of the region in which the lesion is present by increasing the weight for the region similarity between the regions in which the lesions are present and decreasing the weight for the region similarity between the regions in the normal state.

Therefore, in this embodiment, the similarity derivation unit 26 classifies a plurality of types of findings into a finding group (hereinafter, referred to as a background finding group) which becomes the background of, for example, the normal lung and emphysema tendency and a finding group (hereinafter, referred to as a lesion finding group) that becomes lesions, such as a punctate shadow, a ground-glass shadow, and an infiltrative shadow. Then, a weighting coefficient Wj used in a case in which the similarity between the examination image V0 and the case image is derived is calculated using only the findings classified into the lesion finding group. Specifically, the weighting coefficient Wj for each region is calculated by the following Expression (7). In Expression (7), Aj is the size of a region j, and Pv1$ij$ is the finding occupancy of all of the findings classified into the lesion finding group in the region j. In addition, Aj may be the weighting coefficient Wj, or Pv1$ij$ may be the weighting coefficient Wj.

$$Wj = Aj \times Pv1ij \quad (7)$$

The similarity derivation unit 26 calculates a similarity St between the examination image V0 and the case image with the following Expression (8), using the weighting coefficient Wj calculated by Expression (7). In Expression (8), B0 is a value obtained by multiplying the size of the entire lung region by the finding occupancy of all of the findings classified into the lesion finding group in the lung region.

$$St = \Sigma(Wj \times Sj2)/B0 \quad (8)$$

In addition, the importance of a finding which is a lesion varies depending on the type of finding. Therefore, it is preferable to derive the similarity in consideration of the importance of the finding. Therefore, the similarity derivation unit 26 sets the degree of importance Ii for each finding using the following Expression (9). In addition, in Expression (9), i is the type of finding classified into a lesion, and fi is a function that has, as a parameter, the finding occupancy Pvi of each finding classified into a lesion in each divided region of the examination image V0.

$$Ii = fi(Pvi) \quad (9)$$

Here, as illustrated in FIG. 13, the number of digits of the value of the volume is different between a finding with a large size and a finding with a small size. Therefore, it is preferable to reduce the dimensions, for example, by converting the finding occupancy, which is three-dimensional information, into two-dimensional finding occupancy using the function fi. In this case, the difference in the size of the finding is matched with the sense of the doctor. For this reason, as described above, it is preferable to nonlinearly convert a finding which has a small size, but is important using the function fi in order to increase the importance of the finding. Therefore, in this embodiment, the function fi is set as represented by the following Expression (10).

$$fi = a \cdot (b \cdot X + (1-b) \cdot X^c) \quad (10)$$

Further, in Expression (10), a is a constant that determines a difference in the overall importance of each finding. c is a constant that has a value of 1 or less and determines the effect of emphasizing a finding with a small size. b is a constant that determines the degree of the effect by the constant c. In addition, $X = (Pvi)^{2/3}$ is established. The finding occupancy Pv is multiplied by ⅔ to be converted from a three-dimensional value to a two-dimensional value.

The similarity derivation unit 26 sets the degree of importance Iij of each finding classified into a lesion in each divided region by setting the function represented by Expression (10) for each finding and applying the function to Expression (9). Then, the similarity derivation unit 26 calculates the sum of the set degrees of importance Iij in the region and multiplies the sum by the size Aj of the region to calculate a weighting coefficient W1j as represented by the following Expression (11). In addition, Iij may be used as the weighting coefficient W1j.

$$W1j = Aj \times \Sigma Iij \quad (11)$$

Then, the similarity derivation unit 26 calculates the similarity St between the examination image V0 and the case image with the following Expression (12), using the weighting coefficient W1j calculated by Expression (11). In Expression (12), B1 is a value obtained by multiplying the sum of the degrees of importance Iij of all of the findings classified into the lesion finding group in the lung region by the size of the entire lung region.

$$St = \Sigma(W1j \times Sj2)/B1 \quad (12)$$

The search unit 27 performs a search process of searching for a case image similar to the examination image V0 as the similar case image from the case database DB on the basis of the similarity St. First, the case database DB will be described.

A plurality of case images, each of which consists of one or more case slice images, are registered in the case database DB. Specifically, as a classification result of findings for each of the plurality of case images, the feature amount (that is, the second feature amount) is registered so as to be associated with each of the plurality of case images. In this embodiment, in a case in which a new examination image V0 is acquired, the examination image V0 is registered as a new case image in the case database DB.

The search unit 27 searches for a case image similar to the examination image V0 as the similar case image on the basis of the similarities St between the examination image V0 and all of the case images registered in the case database DB. Specifically, the search unit 27 sorts the case images in descending order of the similarity St to create a search result list. FIG. 14 is a diagram illustrating the search result list. As illustrated in FIG. 14, the case images registered in the case database DB are sorted in descending order of the similarity St in a search result list LO. Then, the search unit 27 extracts a predetermined number of top case images sorted in the search result list LO as the similar case images from the case database DB.

Figure 15:
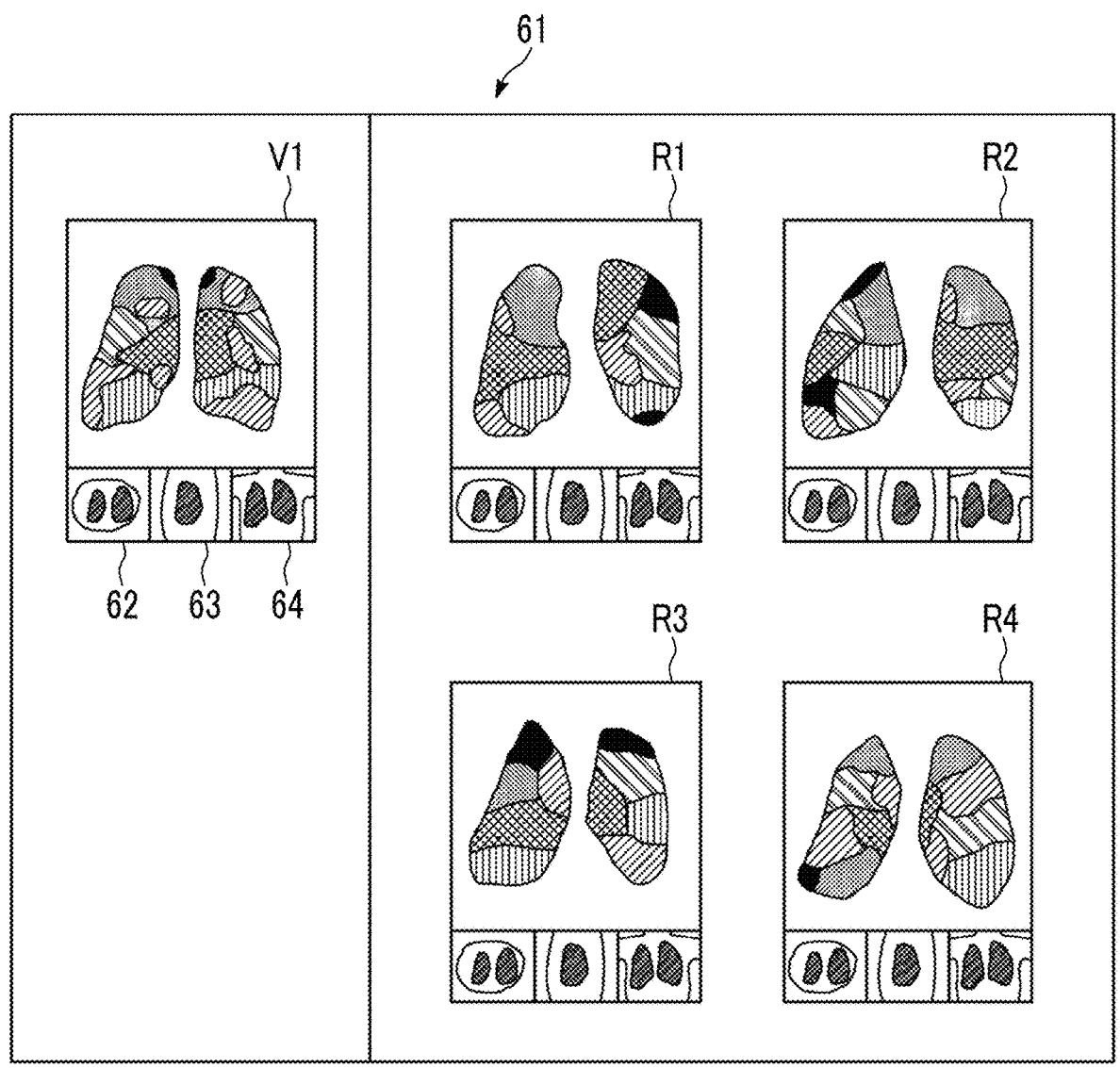
FIG. 15 is a diagram illustrating search results.

The display control unit 28 displays the search results of the search unit 27 on the display unit 14. FIG. 15 is a diagram illustrating the search results. As illustrated in FIG. 15, a labeled examination image V1 and labeled similar case images R1 to R4 are displayed in search results 61. In addition, here, four similar case images R1 to R4 are displayed. However, more similar case images may be displayed.

In FIG. 15, the examination image V1 and the similar case images R1 to R4 are projection images projected by a predetermined projection method. Further, only five types of labeling are illustrated in FIG. 15 for the sake of description. However, in practice, the types of labeling correspond to the types of classified findings. Examination slice images 62 to 64 in three cross sections of an axial cross section, a sagittal cross section, and a coronal cross section are displayed below the examination image V1. In addition, case slice images of the same three cross sections as described above are displayed below each of the similar case images R1 to R4. Further, the slice planes of the examination slice images 62 to 64 displayed below the examination image V1 and the case slice images displayed below the similar case images R1 to R4 can be switched by an operation from the input unit 15.

Figure 16:
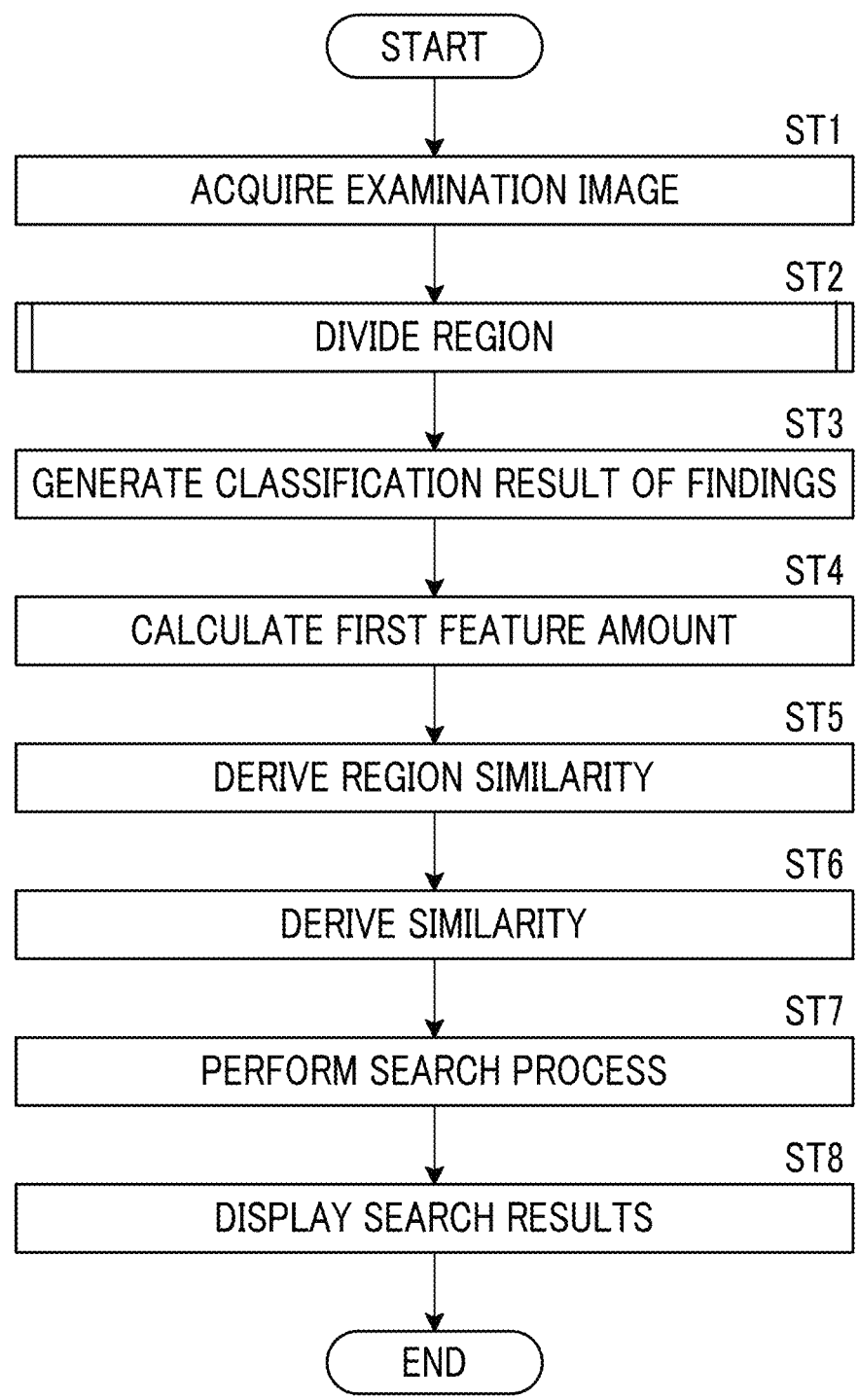
FIG. 16 is a flowchart illustrating a process performed in the first embodiment.

Then, a process performed in the first embodiment will be described. FIG. 16 is a flowchart illustrating the process performed in the first embodiment. First, the image acquisition unit 21 acquires the examination image V0 (Step ST1). The region division unit 22 divides the lung region of the examination image V0 into a plurality of regions (Step ST2).

Figure 17:
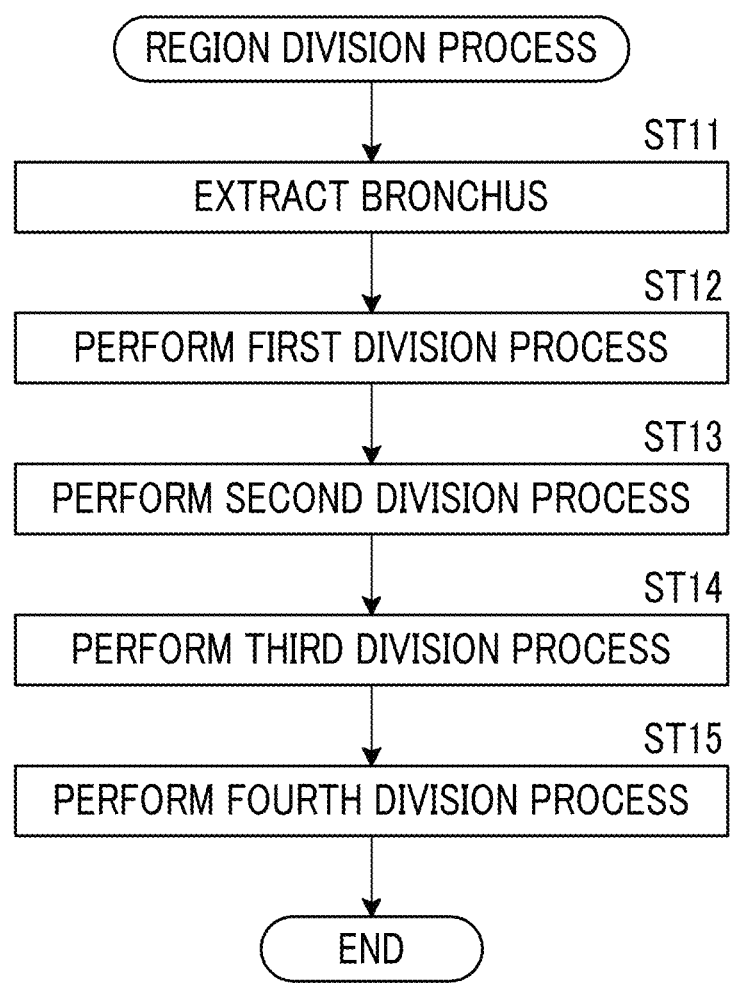
FIG. 17 is a flowchart illustrating a region division process.

FIG. 17 is a flowchart illustrating a region division process. In the region division process, the bronchus extraction unit 30 extracts the structure of the bronchus as a bronchial region from the examination image V0 (Step ST11). Then, the first division unit 31 divides the lung region into a plurality of regions in the vertical direction on the basis of the branch position of the bronchus (a first division process; Step ST12). Further, the second division unit 32 divides the lung region into a central region and a region other than the central region (a second division process; Step ST13). In addition, the third division unit 33 divides the lung region into an outer region and an inner region (a third division process; Step ST14). Then, the fourth division unit 34 divides the lung region into a dorsal region and a ventral region (a fourth division process; Step ST15). Then, the region division process ends.

Returning to FIG. 16, the finding classification unit 23 classifies each pixel of the lung region included in the examination image V0 into at least one finding and generates the classification result of findings (Step ST3). Then, the feature amount calculation unit 24 calculates the first feature amount for each finding classified in the examination image V0 and for each divided region (Step ST4). In addition, the region similarity derivation unit 25 derives the region similarity which is the similarity between the examination image V0 and the case image for each divided region on the basis of the first feature amount for each finding calculated in the examination image V0 and the second feature amount for each finding calculated in advance in the case image (Step ST5). Further, the similarity derivation unit 26 performs a weighting operation for a plurality of region similarities to derive the similarity between the examination image V0 and the case image (Step ST6). In addition, as described above, the similarity derivation unit 26 derives the similarities between the examination image V0 and all of the case images registered in the case database DB. Further, the search unit 27 performs the search process on the basis of the similarities (Step ST7), and the display control unit 28 displays the search results on the display unit 14 (Step ST8). Then, the process ends.

As described above, according to this embodiment, the lung region of the examination image V0 is divided into a plurality of regions, and each pixel of the examination image V0 is classified into at least one finding. In addition, the first feature amount for each finding classified in the examination image V0 is calculated for each divided region. Then, the region similarity between the examination image V0 and the case image is derived for each divided region on the basis of the first feature amount for each finding calculated in the examination image V0 and the second feature amount for each finding calculated in advance in the case image. Furthermore, a weighting operation is performed for a plurality of region similarities using a weighting coefficient corresponding to at least one of the size of each divided region or the size of a specific finding included in each divided region to derive the similarity between the examination image V0 and the case image. According to this embodiment, in accordance with the above, the weighting operation is performed for the region similarity between the divided regions. Therefore, appropriate weighting is performed according to the position and distribution of findings in a target region. As a result, it is possible to appropriately determine the similarity between the examination image V0 and the case image.

Next, a second embodiment of the present disclosure will be described. In the first embodiment, the region similarities are derived for the 13 left regions and the 13 right regions divided by the region division unit 22 to derive the similarity between the examination image V0 and the case image. The second embodiment is different from the first embodiment in that the lung region is divided into a plurality of regions for each region pattern on the basis of a plurality of different types of region patterns and the region similarity is derived for each region pattern. In addition, the configuration of a similarity determination apparatus according to the second embodiment is the same as the configuration of the similarity determination apparatus according to the first embodiment except only the process to be performed. Therefore, the detailed description of the apparatus will be omitted.

Here, in a case in which the onset position of a disease in the lung is a position characteristic of the disease and is in a relatively wide range, it is possible to appropriately derive the similarity between the examination image V0 and the case image even though the lung region is divided by one region pattern as in the first embodiment. However, for a lesion, such as a mass lesion, that develops locally and develops at various positions in the lung region, in a case in which the lesion is present in both the examination image V0 and the case image, but is not present in the corresponding region of the examination image V0 and the case image, the value of the similarity does not increase. As a result, it is difficult to search for a case image similar to the examination image V0.

In general, local lesions that develop locally and diffuse lesions have different features. Therefore, these lesions are classified into different findings. For example, findings, such as ground-glass shadows and reticular shadows, are diffuse lesions, and findings, such as nodular shadows, are local lesions. In the case of the findings classified into the diffuse lesions, the region similarity for each region obtained by more finely dividing the lung region is derived to appropriately derive the similarity between the examination image V0 and the case image. In contrast, in the case of the findings classified into the local lesions, the region similarity for each region obtained by roughly dividing the lung region is derived to appropriately derive the similarity between the examination image V0 and the case image.

Therefore, in the second embodiment, the region similarity is derived by a divided region pattern (hereinafter, referred to as a second region pattern) acquired by only the first division process of the first division unit 31, a divided region pattern (hereinafter, referred to as a third region pattern) acquired by only the second division process of the second division unit 32, a divided region pattern (hereinafter, referred to as a fourth region pattern) acquired by only the third division process of the third division unit 33, and a divided region pattern (hereinafter, referred to as a fifth region pattern) acquired by only the fourth division process of the fourth division unit 34, in addition to the region pattern (hereinafter, referred to as a first region pattern) in which each of the left and right lung regions is divided into 13 regions as in the first embodiment. Further, in the second embodiment, it is assumed that a state in which the left and right lung regions 40L and 40R are not divided at all is also included in one of the region patterns (sixth region pattern).

Here, in the second embodiment, it is not necessary to use all of the first to sixth region patterns, and the left and right lung regions 40L and 40R may be divided by two or more of these region patterns. In addition, one lung region is divided into 13 regions by the first region pattern, is divided into three regions by the second region pattern, is divided into two regions by the third region pattern, is divided into two regions by the fourth region pattern, is divided into two regions by the fifth region pattern, and is divided into one region by the sixth region pattern. Therefore, in a case in which all of the first to sixth region patterns are used, 23 region similarities are derived in one lung region (46 region similarities are derived in left and right lungs).

In the second embodiment, the similarity derivation unit 26 calculates a weighting coefficient W2$j$ for each region for the region similarities based on all of the region patterns, using the following Expression (13). In Expression (13), Iij is the degree of importance of each finding classified into a lesion in each divided region, and PWir is a weighting coefficient for a finding i included in the region divided by a region pattern r. Therefore, Expression (13) calculates the weighting coefficient W2$j$ by calculating the sum of the values obtained by weighting the degrees of importance Iij of the findings for each divided region with the weighting coefficients PWir for the findings i corresponding to the region pattern in the region and multiplying the sum by the size Aj of the region. In addition, the weighting coefficient PWir is a region pattern weighting coefficient. Further, $\Sigma(PWir \times Iij)$ may be used as the weighting coefficient W2$j$.

$$W2j = Aj \times \Sigma(\underline{PWir \times Iij}) \tag{13}$$

FIG. 18 is a diagram illustrating an example of the weighting coefficient PWir. In FIG. 18, FIRST, SECOND, and SIXTH indicate the first region pattern (one lung region is divided into 13 regions), the second region pattern (one lung region is divided into three regions), and the sixth region pattern (one lung region is divided into one region), respectively. As illustrated in FIG. 18, for example, 0.7 is set as the weighting coefficient PWir for the finding of the ground-glass shadow included in the region divided by the first region pattern. In addition, 0.3 is set as the weighting coefficient PWir for the finding of the ground-glass shadow included in the region divided by the second region pattern. Further, 0 is set as the weighting coefficient PWir for the finding of the ground-glass shadow included in the region divided by the sixth region pattern. In a case in which the weighting coefficient PWir is 0, the weighting coefficient W2$j$ calculated by Expression (13) is also 0. In contrast, 0 is set as the weighting coefficient PWir for the finding of the nodular shadow included in the region divided by the first region pattern. In addition, 0.5 is set as the weighting coefficient PWir for the finding of the nodular shadow included in the region divided by the second region pattern. Further, 0.5 is set as the weighting coefficient PWir for the finding of the nodular shadow included in the region divided by the sixth region pattern.

Therefore, in a case in which the weighting coefficient PWir illustrated in FIG. 18 is adopted, in the derivation of the similarity St, a region similarity for a finely divided region is mainly adopted for the findings of the ground-glass shadow and the reticular shadow, and a region similarity for a roughly divided region is mainly adopted for the finding of the nodular shadow. As a result, it is possible to derive the similarity St between the examination image V0 and the case image in consideration of the features of the local lesion and the diffuse lesion.

Then, in the second embodiment, the similarity derivation unit 26 calculates the similarity St between the examination image V0 and the case image with the following Expression (14), using the weighting coefficient W2$j$ calculated by Expression (13). In Expression (14), B3 is a value obtained by multiplying the sum of W2$j$ for all of the findings classified into the lesion finding group in the lung region by the size of the entire lung region.

$$St = \Sigma(W2j \times Sj2)/B3 \tag{14}$$

Further, in the second embodiment, the weighting coefficient PWir may be changed. For example, the weighting coefficient PWir may be changed depending on whether the lesion of interest in the examination image V0 is the local lesion or the diffuse lesion. In this case, preferably, the weighting coefficient PWir can be changed by a change command from the operator through the input unit 15. FIGS. 19 and 20 are diagrams illustrating other examples of the weighting coefficient PWir. The weighting coefficient PWir illustrated in FIG. 19 has a value of 0 for any of the findings in the sixth region pattern. The use of the weighting coefficient PWir makes it possible to appropriately search for a similar case image in a case in which the lesion of interest in the examination image V0 is only the local lesion.

In contrast, the weighting coefficient PWir illustrated in FIG. 20 has a value of 0 for any of the findings in the first region pattern. The use of the weighting coefficient PWir makes it possible to appropriately search for a similar case image in a case in which the lesion of interest in the examination image V0 is only the diffuse lesion.

Further, in each of the above-described embodiments, the region similarity between the corresponding regions of the examination image V0 and the case image is derived. However, the present disclosure is not limited thereto. For example, not only the region similarity between the corresponding regions but also the region similarity with regions other than the corresponding regions may be derived. In a case in which the region similarity with the regions other than the corresponding regions is derived, for example, it is preferable that the weight becomes larger as the region becomes closer to the corresponding region.

In each of the above-described embodiments, a plurality of evaluation values indicating the possibility of each pixel of the examination image V0 being each of a plurality of types of findings are calculated, and each pixel of the examination image V0 is classified into at least one of the plurality of types of findings on the basis of the plurality of evaluation values. However, a finding classification method is not limited to the method using the evaluation values.

Further, in each of the above-described embodiments, the case database DB is stored in the image storage server 3. However, the case database DB may be stored in the storage 13.

Further, in each of the above-described embodiments, the examination image is registered in the case database DB. However, images other than the examination image may be registered as registration target images in the case database.

In each of the above-described embodiments, for example, the following various processors can be used as the hardware structure of processing units performing various processes, such as the image acquisition unit 21, the region division unit 22, the finding classification unit 23, the feature amount calculation unit 24, the region similarity derivation unit 25, the similarity derivation unit 26, the search unit 27, and the display control unit 28. The various processors include a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). In accordance with the above, various processing units are configured by using one or more of the various processors as a hardware structure.

In addition, specifically, an electric circuit (circuitry) obtained by combining circuit elements, such as semiconductor elements, can be used as the hardware structure of the various processors.

EXPLANATION OF REFERENCES

1: similarity determination apparatus
2: three-dimensional imaging apparatus
3: image storage server
4: network
11: CPU
12: memory
13: storage
14: display unit
15: input unit
21: image acquisition unit
22: region division unit
23: finding classification unit
24: feature amount calculation unit
25: region similarity derivation unit
26: similarity derivation unit
27: search unit
28: display control unit
30: bronchus extraction unit
31: first division unit
32: second division unit
33: third division unit
34: fourth division unit
40L: left lung region
40R: right lung region
41: bronchus
50: multi-layer neural network
51: input layer
52: output layer
61: search results
62 to 64: examination slice image
B1, B31: bronchial branch
DB: case database
G1: tomographic image in axial direction
G2: tomographic image in coronal direction
G3: tomographic image in sagittal direction
L0: search result list
R1 to R4: similar case image
V0, V1: examination image

What is claimed is:

1. A similarity determination apparatus for determining a similarity between a first medical image and a second medical image, comprising:
 a processor configured to
 divide a target region of the first medical image into a plurality of regions;
 classify each pixel of the first medical image into at least one finding;
 calculate a first feature amount for each finding classified in the first medical image for each of the divided regions;
 derive a region similarity between the first medical image and the second medical image for each of the divided regions, on the basis of the first feature amount for each finding calculated in the first medical image and a second feature amount for each finding calculated in advance in the second medical image; and
 derive a similarity between the first medical image and the second medical image by performing a weighting operation for a plurality of the region similarities with a weighting coefficient corresponding to at least one of a size of each of the divided regions or a size of a specific finding included in each of the divided regions.

2. The similarity determination apparatus according to claim 1,
 wherein the processor is configured to:
 divide the target region into a plurality of regions for each of a plurality of different types of region patterns, on the basis of the region patterns;

calculate the first feature amount for each of the divided regions for each of the region patterns;

derive the region similarity for each of the divided regions for each of the region patterns, and perform the weighting operation for the region similarities for the plurality of types of region patterns to derive the similarity between the first medical image and the second medical image.

3. The similarity determination apparatus according to claim 2, wherein the processor is configured to perform the weighting operation for the region similarities for the plurality of types of region patterns using the weighting coefficient and a region pattern weighting coefficient corresponding to a type of the finding and a type of the region pattern.

4. The similarity determination apparatus according to claim 3, further comprising:

an input unit configured to receive a command to change the region pattern weighting coefficient, wherein the processor is configured to perform the weighting operation using the weighting coefficient and the changed region pattern weighting coefficient.

5. The similarity determination apparatus according to claim 2, wherein the specific finding is a finding of a lesion.

6. The similarity determination apparatus according to claim 2, wherein the processor includes a discriminator that has been subjected to machine learning so as to classify a plurality of types of the findings, and classifies each pixel of the first medical image into at least one of the plurality of types of findings using the discriminator.

7. The similarity determination apparatus according to claim 2, wherein, in a case in which the first medical image and the second medical image include a lung and the target region is a lung region, the processor is configured to extract a bronchus from the lung region and divides the lung region into a plurality of regions on the basis of a position of the bronchus.

8. The similarity determination apparatus according to claim 1, wherein the specific finding is a finding of a lesion.

9. The similarity determination apparatus according to claim 1, wherein the processor comprises a discriminator that has been subjected to machine learning so as to classify a plurality of types of the findings, and classifies each pixel of the first medical image into at least one of the plurality of types of findings using the discriminator.

10. The similarity determination apparatus according to claim 1, the processor further configured to:

search for the second medical image similar to the first medical image as a similar medical image on the basis of similarities between the first medical image and a plurality of second medical images with reference to a case database in which the plurality of second medical images are registered and the second feature amount for each of the plurality of second medical images are registered so as to be associated with each of the plurality of second medical images.

11. The similarity determination apparatus according to claim 10, the processor further configured to:

display a search result of the similar medical image on a display.

12. The similarity determination apparatus according to claim 1, the processor further configured to:

search for the second medical image similar to the first medical image as a similar medical image on the basis of similarities between the first medical image and a plurality of second medical images with reference to a case database in which the plurality of second medical images are registered and the second feature amount for each of the plurality of second medical images are registered so as to be associated with each of the plurality of second medical images.

13. The similarity determination apparatus according to claim 1, wherein, in a case in which the first medical image and the second medical image include a lung and the target region is a lung region, the processor is configured to extract a bronchus from the lung region and divide the lung region into a plurality of regions on the basis of a position of the bronchus.

14. The similarity determination apparatus according to claim 13, wherein the processor is configured to specify a plurality of branch positions of the bronchus and divide the lung region into a plurality of regions on the basis of the branch positions.

15. The similarity determination apparatus according to claim 14, wherein the processor is configured to divide the lung region into a plurality of regions in a vertical direction on the basis of the branch positions.

16. The similarity determination apparatus according to claim 14, wherein the processor is configured to divide the lung region into a region within a specific distance from a specific branch position among the plurality of branch positions and a region other than the region within the specific distance.

17. The similarity determination apparatus according to claim 13, wherein the processor is further configured to divide the lung region into an outer region and an inner region.

18. The similarity determination apparatus according to claim 13, wherein the processor is further configured to divide the lung region into a dorsal region and a ventral region.

19. A similarity determination method for determining a similarity between a first medical image and a second medical image, the method comprising:

dividing a target region of the first medical image into a plurality of regions;

classifying each pixel of the first medical image into at least one finding;

calculating a first feature amount for each finding classified in the first medical image for each of the divided regions;

deriving a region similarity between the first medical image and the second medical image for each of the divided regions, on the basis of the first feature amount for each finding calculated in the first medical image and a second feature amount for each finding calculated in advance in the second medical image; and deriving a similarity between the first medical image and the second medical image by performing a weighting operation for a plurality of the region similarities with a weighting coefficient corresponding to at least one of a size of each of the divided regions or a size of a specific finding included in each of the divided regions.

20. A non-transitory computer readable recording medium storing a similarity determination program that causes a computer to perform a process of determining a similarity between a first medical image and a second medical image, the program causing the computer to perform:
- a step of dividing a target region of the first medical image into a plurality of regions;
- a step of classifying each pixel of the first medical image into at least one finding;
- a step of calculating a first feature amount for each finding classified in the first medical image for each of the divided regions;
- a step of deriving a region similarity between the first medical image and the second medical image for each of the divided regions, on the basis of the first feature amount for each finding calculated in the first medical image and a second feature amount for each finding calculated in advance in the second medical image; and
- a step of deriving a similarity between the first medical image and the second medical image by performing a weighting operation for a plurality of the region similarities with a weighting coefficient corresponding to at least one of a size of each of the divided regions or a size of a specific finding included in each of the divided regions.

* * * * *